US012599389B2

(12) United States Patent
Dayton et al.

(10) Patent No.: US 12,599,389 B2
(45) Date of Patent: Apr. 14, 2026

(54) MULTI-SIDED CUTTING INSTRUMENT FOR MOBILIZING SMALL BONES IN THE FOOT

(71) Applicant: Treace Medical Concepts, Inc., Ponte Vedra, FL (US)

(72) Inventors: Paul Dayton, Ankeny, IA (US); William T. DeCarbo, Pittsburgh, PA (US); Jody McAleer, Jefferson City, MO (US); Robert D. Santrock, Morgantown, WV (US); Mark Erik Easley, Durham, NC (US); Adriaan Kuyler, Ponte Vedra, FL (US); Bryan Wilcox, St. Augustine, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 353 days.

(21) Appl. No.: 18/173,649

(22) Filed: Feb. 23, 2023

(65) Prior Publication Data

US 2023/0263540 A1     Aug. 24, 2023

Related U.S. Application Data

(60) Provisional application No. 63/313,124, filed on Feb. 23, 2022.

(51) Int. Cl.
*A61B 17/16*          (2006.01)
(52) U.S. Cl.
CPC ................................ *A61B 17/1682* (2013.01)
(58) Field of Classification Search
CPC . A61B 17/1682; A61B 17/32; A61B 17/1659; A61B 17/1604
See application file for complete search history.

(56) References Cited

U.S. PATENT DOCUMENTS

| 3,664,022 A | 5/1972 | Small |
| D234,214 S | 1/1975 | Mcevoy |

(Continued)

FOREIGN PATENT DOCUMENTS

| AU | 2009227957 B2 | 7/2014 |
| CA | 2491824 A1 | 9/2005 |

(Continued)

OTHER PUBLICATIONS

PB Swiss Tools 8126-9-45 Swiss Grip Starby Coin Driver, amazon. com, first available Apr. 9, 2015 [online], [site visited Mar. 19, 2024], Available from internet, URL: https://www.amazon.com/PB-Swiss-PB-8126-SwissGrip-Plastic/dp/BOOVTLR01Q (Year: 2015).

(Continued)

*Primary Examiner* — Zade Coley
*Assistant Examiner* — Diana Jones
(74) *Attorney, Agent, or Firm* — Fredrikson & Byron, P.A.

(57)                    ABSTRACT

An orthopedic cutting instrument can be used to cut and release soft tissue to mobilize a bone for subsequent realignment of the bone. In some examples, the cutting instrument is configured with a handle and a cutting head. The cutting head has multiple cutting surfaces, such as a lead cutting surface and side cutting surfaces extending angularly away from the lead cutting surface. A mirror set of cutting surfaces may be provided on the opposite side of the cutting head. The cutting surfaces may be arranged to allow controlling cutting of soft tissue while limiting inadvertent deep penetration of the cutting instrument. In addition, the cutting surfaces may be arranged to allow back-and-forth cutting movement of the cutting head, which can be useful when working in a tight joint space.

31 Claims, 18 Drawing Sheets

(56) References Cited

U.S. PATENT DOCUMENTS

| | | | |
|---|---|---|---|
| 4,069,824 A | 1/1978 | Weinstock |
| 4,159,716 A | 7/1979 | Borchers |
| 4,187,840 A | 2/1980 | Watanabe |
| D258,932 S | 4/1981 | Graham |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,601,290 A | 7/1986 | Effron et al. |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| D312,954 S | 12/1990 | Wilbanks |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| D340,634 S | 10/1993 | Lipic |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,857,995 A | 1/1999 | Thomas et al. |
| D405,178 S | 2/1999 | Eugene |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | Mcguire |
| 6,030,391 A | 2/2000 | Brainard et al. |
| 6,056,764 A | 5/2000 | Smith |
| 6,139,559 A | 10/2000 | Nordan et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| D487,559 S | 3/2004 | Callander |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 6,964,645 B1 | 11/2005 | Smits |
| 7,018,383 B2 | 3/2006 | McGuire |
| 7,033,361 B2 | 4/2006 | Collazo |
| 7,097,647 B2 | 8/2006 | Segler et al. |
| 7,112,204 B2 | 9/2006 | Justin et al. |
| 7,153,310 B2 | 12/2006 | Ralph et al. |
| D535,747 S | 1/2007 | Isogimi |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| D575,128 S | 8/2008 | Clampitt, Jr. et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| D639,631 S | 6/2011 | Kempker et al. |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,668 S | 9/2012 | Present |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |

(56)                References Cited

U.S. PATENT DOCUMENTS

| 8,337,503 | B2 | 12/2012 | Lian |
| 8,343,159 | B2 | 1/2013 | Bennett |
| 8,377,105 | B2 | 2/2013 | Buescher |
| D679,395 | S | 4/2013 | Wright et al. |
| D679,397 | S | 4/2013 | Packard et al. |
| 8,409,209 | B2 | 4/2013 | Ammann et al. |
| 8,435,246 | B2 | 5/2013 | Fisher et al. |
| 8,475,462 | B2 | 7/2013 | Thomas et al. |
| 8,496,662 | B2 | 7/2013 | Novak et al. |
| 8,518,045 | B2 | 8/2013 | Szanto |
| 8,523,870 | B2 | 9/2013 | Green, II et al. |
| 8,529,571 | B2 | 9/2013 | Horan et al. |
| 8,540,777 | B2 | 9/2013 | Ammann et al. |
| 8,545,508 | B2 | 10/2013 | Collazo |
| D694,884 | S | 12/2013 | Mooradian et al. |
| D695,402 | S | 12/2013 | Dacosta et al. |
| 8,652,142 | B2 | 2/2014 | Geissler |
| 8,657,820 | B2 | 2/2014 | Kubiak et al. |
| D701,303 | S | 3/2014 | Cook |
| 8,672,945 | B2 | 3/2014 | Lavallee et al. |
| 8,696,716 | B2 | 4/2014 | Kartalian et al. |
| 8,702,715 | B2 | 4/2014 | Ammann et al. |
| D705,929 | S | 5/2014 | Frey |
| 8,715,363 | B2 | 5/2014 | Ratron et al. |
| 8,728,084 | B2 | 5/2014 | Berelsman et al. |
| 8,758,354 | B2 | 6/2014 | Habegger et al. |
| 8,764,760 | B2 | 7/2014 | Metzger et al. |
| 8,764,763 | B2 | 7/2014 | Wong et al. |
| 8,771,279 | B2 | 7/2014 | Philippon et al. |
| 8,777,948 | B2 | 7/2014 | Bernsteiner |
| 8,784,427 | B2 | 7/2014 | Fallin et al. |
| 8,784,457 | B2 | 7/2014 | Graham |
| 8,795,286 | B2 | 8/2014 | Sand et al. |
| 8,801,727 | B2 | 8/2014 | Chan et al. |
| 8,808,303 | B2 | 8/2014 | Stemniski et al. |
| 8,828,012 | B2 | 9/2014 | May et al. |
| 8,858,602 | B2 | 10/2014 | Weiner et al. |
| 8,882,778 | B2 | 11/2014 | Ranft |
| 8,882,816 | B2 | 11/2014 | Kartalian et al. |
| 8,888,785 | B2 | 11/2014 | Ammann et al. |
| D718,898 | S | 12/2014 | Ismiel et al. |
| D720,456 | S | 12/2014 | Dacosta et al. |
| 8,900,247 | B2 | 12/2014 | Tseng et al. |
| 8,906,026 | B2 | 12/2014 | Ammann et al. |
| 8,945,132 | B2 | 2/2015 | Plassy et al. |
| 8,998,903 | B2 | 4/2015 | Price et al. |
| 8,998,904 | B2 | 4/2015 | Zeetser et al. |
| 9,011,507 | B2 | 4/2015 | Schelling |
| D728,352 | S | 5/2015 | Martinson |
| 9,023,052 | B2 | 5/2015 | Lietz et al. |
| 9,044,250 | B2 | 6/2015 | Olsen et al. |
| 9,060,822 | B2 | 6/2015 | Lewis et al. |
| 9,089,376 | B2 | 7/2015 | Medoff et al. |
| 9,101,421 | B2 | 8/2015 | Blacklidge |
| 9,107,715 | B2 | 8/2015 | Blitz et al. |
| 9,113,920 | B2 | 8/2015 | Ammann et al. |
| D740,424 | S | 10/2015 | Dacosta et al. |
| D765,844 | S | 9/2016 | DaCosta |
| D766,434 | S | 9/2016 | DaCosta |
| D766,437 | S | 9/2016 | DaCosta |
| D766,438 | S | 9/2016 | DaCosta |
| D766,439 | S | 9/2016 | DaCosta |
| 9,452,057 | B2 | 9/2016 | Dacosta et al. |
| 9,522,023 | B2 | 12/2016 | Haddad et al. |
| 9,592,084 | B2 | 3/2017 | Grant |
| 9,750,538 | B2 | 9/2017 | Soffiatti et al. |
| 9,785,747 | B2 | 10/2017 | Geebelen |
| D813,394 | S | 3/2018 | Dacosta et al. |
| 9,980,760 | B2 | 5/2018 | Dacosta et al. |
| 10,028,750 | B2 | 7/2018 | Rose |
| 10,064,631 | B2 | 9/2018 | Dacosta et al. |
| 10,159,499 | B2 | 12/2018 | Dacosta et al. |
| 10,292,713 | B2 | 5/2019 | Fallin et al. |
| 10,327,829 | B2 | 6/2019 | Dacosta et al. |
| 10,376,268 | B2 | 8/2019 | Fallin et al. |
| 10,470,779 | B2 | 11/2019 | Fallin et al. |
| D885,572 | S | 5/2020 | Sekikawa et al. |
| 10,779,867 | B2 | 9/2020 | Penzimer et al. |
| 10,856,886 | B2 | 12/2020 | Dacosta et al. |
| 10,856,918 | B2 | 12/2020 | Dacosta |
| D911,799 | S | 3/2021 | Sweitzer et al. |
| 10,939,939 | B1 | 3/2021 | Gil et al. |
| 11,083,622 | B2 | 8/2021 | Cady et al. |
| 11,304,705 | B2 | 4/2022 | Fallin et al. |
| D1,029,258 | S | 5/2024 | Stroh |
| D1,059,591 | S | 1/2025 | Aarsheim et al. |
| D1,059,592 | S | 1/2025 | Lambert |
| D1,065,532 | S | 3/2025 | Wright |
| 2002/0099381 | A1 | 7/2002 | Maroney |
| 2002/0107519 | A1 | 8/2002 | Dixon et al. |
| 2002/0165552 | A1 | 11/2002 | Duffner |
| 2002/0198531 | A1 | 12/2002 | Millard et al. |
| 2004/0010259 | A1 | 1/2004 | Keller et al. |
| 2004/0039394 | A1 | 2/2004 | Conti et al. |
| 2004/0097946 | A1 | 5/2004 | Dietzel et al. |
| 2004/0138669 | A1 | 7/2004 | Horn |
| 2005/0004587 | A1 | 1/2005 | Matsutani et al. |
| 2005/0004676 | A1 | 1/2005 | Schon et al. |
| 2005/0059978 | A1 | 3/2005 | Sherry et al. |
| 2005/0070909 | A1 | 3/2005 | Egger et al. |
| 2005/0075641 | A1 | 4/2005 | Singhatat et al. |
| 2005/0101961 | A1 | 5/2005 | Huebner et al. |
| 2005/0149042 | A1 | 7/2005 | Metzger |
| 2005/0228389 | A1 | 10/2005 | Stiernborg |
| 2005/0251147 | A1 | 11/2005 | Novak |
| 2005/0267482 | A1 | 12/2005 | Hyde, Jr. |
| 2005/0273112 | A1 | 12/2005 | McNamara |
| 2006/0058824 | A1 | 3/2006 | Kozlowski |
| 2006/0129163 | A1 | 6/2006 | McGuire |
| 2006/0206044 | A1 | 9/2006 | Simon |
| 2006/0217733 | A1 | 9/2006 | Plassky et al. |
| 2006/0229621 | A1 | 10/2006 | Cadmus |
| 2006/0241607 | A1 | 10/2006 | Myerson et al. |
| 2006/0241608 | A1 | 10/2006 | Myerson et al. |
| 2006/0264961 | A1 | 11/2006 | Murray-Brown |
| 2007/0010818 | A1 | 1/2007 | Stone et al. |
| 2007/0123857 | A1 | 5/2007 | Deffenbaugh et al. |
| 2007/0233138 | A1 | 10/2007 | Figueroa et al. |
| 2007/0265634 | A1 | 11/2007 | Weinstein |
| 2007/0276383 | A1 | 11/2007 | Rayhack |
| 2008/0009863 | A1 | 1/2008 | Bond et al. |
| 2008/0015603 | A1 | 1/2008 | Collazo |
| 2008/0039850 | A1 | 2/2008 | Rowley et al. |
| 2008/0091197 | A1 | 4/2008 | Coughlin |
| 2008/0140081 | A1 | 6/2008 | Heavener et al. |
| 2008/0147073 | A1 | 6/2008 | Ammann et al. |
| 2008/0172054 | A1 | 7/2008 | Claypool et al. |
| 2008/0195215 | A1 | 8/2008 | Morton |
| 2008/0208252 | A1 | 8/2008 | Holmes |
| 2008/0262500 | A1 | 10/2008 | Collazo |
| 2008/0269908 | A1 | 10/2008 | Warburton |
| 2008/0288004 | A1 | 11/2008 | Schendel |
| 2009/0036893 | A1 | 2/2009 | Kartalian et al. |
| 2009/0036931 | A1 | 2/2009 | Pech et al. |
| 2009/0054899 | A1 | 2/2009 | Ammann et al. |
| 2009/0093849 | A1 | 4/2009 | Grabowski |
| 2009/0105767 | A1 | 4/2009 | Reiley |
| 2009/0112212 | A1 | 4/2009 | Murray et al. |
| 2009/0118733 | A1 | 5/2009 | Orsak et al. |
| 2009/0198244 | A1 | 8/2009 | Leibel |
| 2009/0198279 | A1 | 8/2009 | Zhang et al. |
| 2009/0216089 | A1 | 8/2009 | Davidson |
| 2009/0222047 | A1 | 9/2009 | Graham |
| 2009/0254092 | A1 | 10/2009 | Albiol Llorach |
| 2009/0254126 | A1 | 10/2009 | Orbay et al. |
| 2009/0287309 | A1 | 11/2009 | Walch et al. |
| 2010/0069910 | A1 | 3/2010 | Hasselman |
| 2010/0121334 | A1 | 5/2010 | Couture et al. |
| 2010/0130981 | A1 | 5/2010 | Richards |
| 2010/0152782 | A1 | 6/2010 | Stone et al. |
| 2010/0168799 | A1 | 7/2010 | Schumer |
| 2010/0185245 | A1 | 7/2010 | Paul et al. |
| 2010/0234849 | A1* | 9/2010 | Bouadi .......... A61B 17/320708 |
| | | | 606/84 |

(56)                References Cited

U.S. PATENT DOCUMENTS

| | | | |
|---|---|---|---|
| 2010/0249779 A1 | 9/2010 | Hotchkiss et al. | |
| 2010/0256687 A1 | 10/2010 | Neufeld et al. | |
| 2010/0318088 A1 | 12/2010 | Warne et al. | |
| 2010/0324556 A1 | 12/2010 | Tyber et al. | |
| 2011/0004214 A1* | 1/2011 | Skaggs | A61B 17/1671 |
| | | | 606/84 |
| 2011/0004241 A1* | 1/2011 | Wintermantel | C08G 18/4812 |
| | | | 156/331.7 |
| 2011/0009865 A1 | 1/2011 | Orfaly | |
| 2011/0093084 A1 | 4/2011 | Morton | |
| 2011/0118739 A1 | 5/2011 | Tyber et al. | |
| 2011/0144676 A1 | 6/2011 | Yamaguchi et al. | |
| 2011/0178524 A1 | 7/2011 | Lawrence et al. | |
| 2011/0213372 A1* | 9/2011 | Keefer | A61B 17/1735 |
| | | | 606/85 |
| 2011/0245835 A1 | 10/2011 | Dodds et al. | |
| 2011/0288550 A1 | 11/2011 | Orbay et al. | |
| 2011/0301648 A1 | 12/2011 | Lofthouse et al. | |
| 2012/0016426 A1 | 1/2012 | Robinson | |
| 2012/0065689 A1 | 3/2012 | Prasad et al. | |
| 2012/0078258 A1 | 3/2012 | Lo et al. | |
| 2012/0123420 A1 | 5/2012 | Honiball | |
| 2012/0123484 A1 | 5/2012 | Lietz et al. | |
| 2012/0130376 A1 | 5/2012 | Loring et al. | |
| 2012/0130382 A1 | 5/2012 | Iannotti et al. | |
| 2012/0130383 A1 | 5/2012 | Budoff | |
| 2012/0184961 A1 | 7/2012 | Johannaber | |
| 2012/0185056 A1 | 7/2012 | Warburton | |
| 2012/0191199 A1 | 7/2012 | Raemisch | |
| 2012/0239045 A1 | 9/2012 | Li | |
| 2012/0253350 A1 | 10/2012 | Anthony et al. | |
| 2012/0265301 A1 | 10/2012 | Demers et al. | |
| 2012/0277745 A1 | 11/2012 | Lizee | |
| 2012/0303033 A1 | 11/2012 | Weiner et al. | |
| 2012/0330135 A1 | 12/2012 | Millahn et al. | |
| 2013/0012949 A1 | 1/2013 | Fallin et al. | |
| 2013/0035694 A1 | 2/2013 | Grimm et al. | |
| 2013/0085499 A1 | 4/2013 | Lian | |
| 2013/0085502 A1 | 4/2013 | Harrold | |
| 2013/0096563 A1 | 4/2013 | Meade et al. | |
| 2013/0131821 A1 | 5/2013 | Cachia | |
| 2013/0150900 A1 | 6/2013 | Haddad et al. | |
| 2013/0150903 A1 | 6/2013 | Vincent | |
| 2013/0158556 A1 | 6/2013 | Jones et al. | |
| 2013/0165936 A1 | 6/2013 | Myers | |
| 2013/0165938 A1 | 6/2013 | Chow et al. | |
| 2013/0172942 A1 | 7/2013 | Lewis et al. | |
| 2013/0184714 A1 | 7/2013 | Kaneyama et al. | |
| 2013/0190765 A1 | 7/2013 | Harris et al. | |
| 2013/0190766 A1 | 7/2013 | Harris et al. | |
| 2013/0204259 A1 | 8/2013 | Zajac | |
| 2013/0226248 A1 | 8/2013 | Hatch et al. | |
| 2013/0226252 A1 | 8/2013 | Mayer | |
| 2013/0231668 A1 | 9/2013 | Olsen et al. | |
| 2013/0237987 A1 | 9/2013 | Graham | |
| 2013/0237989 A1 | 9/2013 | Bonutti | |
| 2013/0267956 A1 | 10/2013 | Terrill et al. | |
| 2013/0310836 A1 | 11/2013 | Raub et al. | |
| 2013/0325019 A1 | 12/2013 | Thomas et al. | |
| 2013/0325076 A1 | 12/2013 | Palmer et al. | |
| 2013/0331845 A1 | 12/2013 | Horan et al. | |
| 2013/0338785 A1 | 12/2013 | Wong | |
| 2014/0005672 A1 | 1/2014 | Edwards et al. | |
| 2014/0025127 A1 | 1/2014 | Richter | |
| 2014/0039501 A1 | 2/2014 | Schickendantz et al. | |
| 2014/0039561 A1 | 2/2014 | Weiner et al. | |
| 2014/0046387 A1 | 2/2014 | Waizenegger | |
| 2014/0074099 A1 | 3/2014 | Vigneron et al. | |
| 2014/0074101 A1 | 3/2014 | Collazo | |
| 2014/0094861 A1 | 4/2014 | Fallin | |
| 2014/0094924 A1 | 4/2014 | Hacking et al. | |
| 2014/0135775 A1 | 5/2014 | Maxson et al. | |
| 2014/0163563 A1 | 6/2014 | Reynolds et al. | |
| 2014/0171953 A1 | 6/2014 | Gonzalvez et al. | |
| 2014/0180342 A1 | 6/2014 | Lowery et al. | |
| 2014/0188139 A1 | 7/2014 | Fallin et al. | |
| 2014/0194884 A1 | 7/2014 | Martin et al. | |
| 2014/0194999 A1 | 7/2014 | Orbay et al. | |
| 2014/0207144 A1 | 7/2014 | Lee et al. | |
| 2014/0249537 A1 | 9/2014 | Wong et al. | |
| 2014/0257308 A1 | 9/2014 | Johannaber | |
| 2014/0257509 A1 | 9/2014 | Dacosta et al. | |
| 2014/0276815 A1 | 9/2014 | Riccione | |
| 2014/0276853 A1 | 9/2014 | Long et al. | |
| 2014/0276968 A1 | 9/2014 | Miksza et al. | |
| 2014/0277176 A1 | 9/2014 | Buchanan et al. | |
| 2014/0277214 A1 | 9/2014 | Helenbolt et al. | |
| 2014/0288562 A1 | 9/2014 | Von Zabern et al. | |
| 2014/0296995 A1 | 10/2014 | Reiley et al. | |
| 2014/0303621 A1 | 10/2014 | Gerold et al. | |
| 2014/0336658 A1 | 11/2014 | Luna et al. | |
| 2014/0343555 A1 | 11/2014 | Russi et al. | |
| 2014/0350561 A1 | 11/2014 | Dacosta et al. | |
| 2015/0032168 A1 | 1/2015 | Orsak et al. | |
| 2015/0045801 A1 | 2/2015 | Axelson, Jr. et al. | |
| 2015/0045839 A1 | 2/2015 | Dacosta et al. | |
| 2015/0051650 A1 | 2/2015 | Verstreken et al. | |
| 2015/0057667 A1 | 2/2015 | Ammann et al. | |
| 2015/0066094 A1 | 3/2015 | Prandi et al. | |
| 2015/0112446 A1 | 4/2015 | Melamed et al. | |
| 2015/0119944 A1 | 4/2015 | Geldwert | |
| 2015/0142064 A1 | 5/2015 | Perez et al. | |
| 2015/0150608 A1 | 6/2015 | Sammarco | |
| 2015/0182273 A1 | 7/2015 | Stemniski et al. | |
| 2015/0223851 A1 | 8/2015 | Hill et al. | |
| 2015/0245858 A1 | 9/2015 | Weiner et al. | |
| 2016/0015426 A1 | 1/2016 | Dayton | |
| 2016/0022315 A1 | 1/2016 | Soffiatti et al. | |
| 2016/0135858 A1 | 5/2016 | Dacosta et al. | |
| 2016/0151165 A1 | 6/2016 | Fallin et al. | |
| 2016/0175089 A1 | 6/2016 | Fallin et al. | |
| 2016/0192950 A1 | 7/2016 | Dayton et al. | |
| 2016/0192970 A1 | 7/2016 | Dayton et al. | |
| 2016/0199076 A1 | 7/2016 | Fallin et al. | |
| 2016/0213384 A1 | 7/2016 | Fallin et al. | |
| 2016/0235414 A1 | 8/2016 | Hatch et al. | |
| 2016/0242791 A1 | 8/2016 | Fallin et al. | |
| 2016/0256204 A1 | 9/2016 | Patel et al. | |
| 2016/0324532 A1 | 11/2016 | Montoya et al. | |
| 2016/0338697 A1 | 11/2016 | Biedermann et al. | |
| 2016/0354127 A1 | 12/2016 | Lundquist et al. | |
| 2017/0014143 A1 | 1/2017 | Dayton et al. | |
| 2017/0014173 A1 | 1/2017 | Smith et al. | |
| 2017/0042598 A1 | 2/2017 | Santrock et al. | |
| 2017/0042599 A1 | 2/2017 | Bays et al. | |
| 2017/0079669 A1 | 3/2017 | Bays et al. | |
| 2017/0143511 A1 | 5/2017 | Cachia | |
| 2017/0164989 A1 | 6/2017 | Weiner et al. | |
| 2017/0231643 A1* | 8/2017 | Victor | A61B 17/164 |
| | | | 606/80 |
| 2018/0132868 A1 | 5/2018 | Dacosta et al. | |
| 2018/0289379 A1 | 10/2018 | Dacosta et al. | |
| 2018/0344334 A1 | 12/2018 | Kim et al. | |
| 2020/0015874 A1 | 1/2020 | Hartson et al. | |
| 2020/0229828 A1 | 7/2020 | Wagner et al. | |
| 2020/0237387 A1 | 7/2020 | Luttrell et al. | |
| 2020/0330109 A1 | 10/2020 | Woodard et al. | |
| 2022/0257267 A1 | 8/2022 | Decarbo et al. | |
| 2023/0201543 A1 | 6/2023 | Simopoulos | |

FOREIGN PATENT DOCUMENTS

| | | | |
|---|---|---|---|
| CA | 2854997 A1 | 5/2013 | |
| CH | 695846 A5 | 9/2006 | |
| CN | 2930668 Y | 8/2007 | |
| CN | 201558162 U | 8/2010 | |
| CN | 201572172 U | 9/2010 | |
| CN | 201586060 U | 9/2010 | |
| CN | 201912210 U | 8/2011 | |
| CN | 101237835 B | 11/2012 | |
| CN | 202801773 U | 3/2013 | |
| CN | 103462675 A | 12/2013 | |
| CN | 103505276 A | 1/2014 | |
| CN | 203458450 U | 3/2014 | |

(56) References Cited

FOREIGN PATENT DOCUMENTS

| | | | |
|---|---|---|---|
| CN | 103735306 | A | 4/2014 |
| CN | 102860860 | B | 5/2014 |
| CN | 203576647 | U | 5/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124772 | A1 | 12/2009 |
| EP | 2124832 | B1 | 8/2012 |
| EP | 2632349 | A1 | 9/2013 |
| EP | 2665428 | A1 | 11/2013 |
| EP | 2742878 | A1 | 6/2014 |
| EP | 2750617 | A1 | 7/2014 |
| EP | 2849684 | A1 | 3/2015 |
| EP | 2624764 | B1 | 12/2015 |
| EP | 3023068 | A2 | 5/2016 |
| FR | 2362616 | A1 | 3/1978 |
| FR | 2764183 | B1 | 11/1999 |
| FR | 2953120 | B1 | 1/2012 |
| FR | 3030221 | A1 | 6/2016 |
| GB | 2154143 | A | 9/1985 |
| GB | 2154144 | A | 9/1985 |
| GB | 2334214 | B | 1/2003 |
| IN | 200903719 | P1 | 6/2009 |
| IN | 200904479 | P2 | 5/2010 |
| IN | 140/DELNP/2012 | P1 | 2/2013 |
| IN | 2004/KOLNP/2013 | P2 | 11/2013 |
| JP | S635739 | A | 1/1988 |
| JP | H0531116 | A | 2/1993 |
| JP | 2004174265 | A | 6/2004 |
| JP | 2006158972 | A | 6/2006 |
| JP | 4134243 | B2 | 8/2008 |
| JP | 2008537498 | A | 9/2008 |
| JP | 4162380 | B2 | 10/2008 |
| JP | 2011092405 | A | 5/2011 |
| JP | 2011523889 | A | 8/2011 |
| JP | 4796943 | B2 | 10/2011 |
| JP | 5466647 | B2 | 4/2014 |
| JP | 2014511207 | A | 5/2014 |
| JP | 2014521384 | A | 8/2014 |
| JP | 5628875 | B2 | 11/2014 |
| KR | 100904142 | B1 | 6/2009 |
| MD | 756 | Z | 11/2014 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009029798 | A1 | 3/2009 |
| WO | 2009032101 | A2 | 3/2009 |
| WO | 2011037885 | A1 | 3/2011 |
| WO | 2012029008 | A1 | 3/2012 |
| WO | 2013090392 | A1 | 6/2013 |
| WO | 2013134387 | A1 | 9/2013 |
| WO | 2013169475 | A1 | 11/2013 |
| WO | 2014020561 | A1 | 2/2014 |
| WO | 2014022055 | A1 | 2/2014 |
| WO | 2014035991 | A1 | 3/2014 |
| WO | 2014085882 | A1 | 6/2014 |
| WO | 2014147099 | A1 | 9/2014 |
| WO | 2014152219 | A2 | 9/2014 |
| WO | 2014152535 | A1 | 9/2014 |
| WO | 2014177783 | A1 | 11/2014 |
| WO | 2014200017 | A1 | 12/2014 |
| WO | 2015094409 | A1 | 6/2015 |
| WO | 2015105880 | A1 | 7/2015 |
| WO | 2015127515 | A2 | 9/2015 |
| WO | 2016134160 | A1 | 8/2016 |
| WO | 2020180598 | A1 | 9/2020 |

OTHER PUBLICATIONS

Lapiplasty, SpeedRelease and TriTome Sales Sheet, lapiplasty.com, first available 2022 [online], [site visited Mar. 19, 2024], Available from internet, URL: https://www.lapiplasty.com/uploads/2022/08/M1969B_SpeedRelease-and-TriTome-TM-SalesSheet.pdf (Year: 2022).

Straight Punch Cutter, amazon.com, first available Sep. 6, 2023 [online], [site visited Mar. 19, 2024], Available from internet, URL: https://www.amazon.com/Straight-Hardness-Incisive-Leather-Punches/dp/B0CHF122VF (Year: 2023).

2 C.S. Osborne Upholstery Tools Staple Remover & Lifter, amazon.com, first available Apr. 21, 2024 [online], [site visited Mar. 19, 2024], Available from internet, URL: https://www.amazon.com/Osborne-Upholstery-Staple-Remover-Lifter/dp/B00JU51704 (Year: 2024).

Precision Bull Nose Replacement Blade, woodworkingshop.com, [online], [site visited Mar. 19, 2024], Available from internet, URL: https://www.woodworkingshop.com/producUWK41900/ (Year: 2024).

Stanley General Purpose Keystone Slotted Screwdriver, grainger.com, [online], [site visited Mar. 19, 2024], Available from internet, URL: https://www.grainger.com/producU6R529 (Year: 2024).

Shard Microsurgical Blades, ad-surgical. com, first reviewed May 26, 2022 [online], [site visited Mar. 19, 2024], Available from internet, https://ad-surgical.com/shard-microsurgical-blades/?sku=A600-M91 (Year: 2022).

Steel Offset Hand Sets, trowandholden.com, [online], [site visited Mar. 19, 2024], Available from internet, URL: https://trowandholden.com/steel-offset-hand-sets.html (Year: 2024).

International Search Report and Written Opinion in PCT/US2023/063162; mail date Oct. 11, 2023; 11 pages.

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

Groves, "Operative Report," St. Tammany Parish Hospital, Date of Procedure, Mar. 26, 2014, 2 pages.

D'Amico et al., "Motion of the First Ray: Clarification Through Investigation," Journal of the American Podiatry Association, vol. 69, No. 1, Jan. 1979, pp. 17-23.

Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Mizuno et al., "Detorsion Osteotomy of the First Metatarsal Bone in Hallux Valgus," Japanese Orthopaedic Association, Tokyo, 1956; 30:813-819.

Eustace et al., "Hallux valgus, first metatarsal pronation and collapse of the medial longitudinal arch—a radiological correlation," Skeletal Radiology, vol. 23, 1994, pp. 191-194.

Collan et al., "The biomechanics of the first metatarsal bone in hallux valgus: A preliminary study utilizing a weight bearing extremity CT," Foot and Ankle Surgery, vol. 19, 2013, pp. 155-161.

Le et al., "Tarsometatarsal Arthrodesis," Operative Techniques in Foot and Ankle Surgery, Section II, Chapter 40, 2011, pp. 281-285.

Coetzee et al., "Revision Hallux Valgus Correction," Operative Techniques in Foot and Ankle Surgery, Section I, Chapter 15, 2011, pp. 84-96.

"Foot and Ankle Instrument Set," Smith & Nephew, 2013, 2 pages.

(56)                    References Cited

OTHER PUBLICATIONS

"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.

"Reconstructive Surgery of the Foot & Ankle," The Podiatry Institute, Update 2015, Conference Program, May 2015, 28 pages.

"Speed Continuous Active Compression Implant," BioMedical Enterprises, Inc., A120-029 Rev. 3, 2013, 4 pages.

"Visionaire: Patient Matched Cutting Blocks Surgical Procedure," Smith & Nephew, Inc., 2009, 2 pages.

Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.

Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.

Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.

Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.

Coughlin, "Fixation of the Lapidus Arthrodesis with a Plantar Interfragmentary Screw and Medial Low Profile Locking Plate," Orthopaedics and Traumatology, vol. 7, 1999, pp. 133-143.

Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

Didomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.

Fallin et al., US Provisional Application Entitled Indexed Tri-Planar Osteotomy Guide and Method, U.S. Appl. No. 62/118,378, filed Feb. 19, 2015, 62 pages.

Fishco, "A Straightforward Guide to the Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Gerard et al., "The Modified Lapidus Procedure," Orthopedics, vol. 31, No. 3, Mar. 2008, 7 pages.

Giannoudis et al., "Hallux Valgus Correction," Practical Procedures in Elective Orthopaedic Surgery, Pelvis and Lower Extremity, Chapter 38, 2012, 22 pages.

Greiner, "The Jargon of Pedal Movements," Foot & Ankle International, vol. 28, No. 1, Jan. 2007, pp. 109-125.

Groves, "Functional Position Joint Sectioning: Pre-Load Method for Lapidus Arthrodesis," The Podiatry Institute, Update 2015, Chapter 6, 2015, pp. 23-29.

Hardy et al., "Observations on Hallux Valgus," The Journal of Bone and Joint Surgery, vol. 33B, No. 3, Aug. 1951, pp. 376-391.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Integra, "Integra Large Qwix Positioning and Fixation Screw, Surgical Technique," 2012, 16 pages.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Myerson, "Cuneiform-Metatarsal Arthrodesis," The Foot and Ankle, Chapter 9, 1997, pp. 107-117.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Schon et al., "Cuneiform-Metatarsal Arthrodesis for Hallux Valgus," The Foot and Ankle, Second Edition, Chapter 8, 2002, pp. 99-117.

Sokoloff, "Lapidus Procedure," Textbook of Bunion Surgery, Chapter 15, 1981, pp. 277-287.

Stamatis et al., "Mini Locking Plate as "Medial Buttress" for Oblique Osteotomy for Hallux Valgus," Foot & Ankle International, vol. 31, No. 10, Oct. 2010, pp. 920-922.

Stewart, "Use for BME Speed Nitinol Staple Fixation for the Lapidus Procedure," date unknown, 1 page.

Wukich et al., "Hypermobility of the First Tarsometatarsal Joint," Foot and Ankle Clinics, vol. 10, No. 1, Mar. 2005, pp. 157-166.

Dayton et al., "Biwinged Excision for Round Pedal Lesions," The Journal of Foot and Ankle Surgery, vol. 35, No. 3, 1996, pp. 244-249.

Dayton et al., "Medial Incision Approach to the First Metatarsophalangeal Joint," The Journal of Foot and Ankle Surgery, vol. 40, No. 6, Nov./Dec. 2001, pp. 414-417.

Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.

Dayton et al., "Use of the Z Osteotomy for Tailor Bunionectomy," The Journal of Foot and Ankle Surgery, vol. 42, No. 3, May/Jun. 2003, pp. 167-169.

Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

Nagy et al., "The AO Ulnar Shortening Osteotomy System Indications and Surgical Technique," Journal of Wrist Surgery, vol. 3, No. 2, 2014, pp. 91-97.

NexFix from Nexa Orthopedics, MetaFix I from Merete Medical, Inc. and the BioPro Lower Extremities from BioPro, found in Foot & Ankle International Journal, vol. 28, No. 1, Jan. 2007, 4 pages.

Odenbring et al., "A guide instrument for high tibial osteotomy," Acta Orthopaedica Scandinavica, vol. 60, No. 4, 1989, pp. 449-451.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

"Patient to Patient Precision, Accu-Cut, Osteotomy Guide System," BioPro, Foot & Ankle International Journal, vol. 23, No. 8, Aug. 2002, 2 pages.

(56) References Cited

OTHER PUBLICATIONS

Peters et al., "Flexor Hallucis Longus Tendon Laceration as a Complication of Total Ankle Arthroplasty," Foot & Ankle International, vol. 34, No. 1, 2013, pp. 148-149.

"Prophecy Inbone Preoperative Navigation Guides," Wright Medical Technology, Inc., Nov. 2013, 6 pages.

"Rayhack Ulnar Shortening Generation II Low-Profile Locking System Surgical Technique," Wright Medical Technology, Inc., Dec. 2013, 20 pages.

Rx-Fix Mini Rail External Fixator, Wright Medical Technology, Brochure, Aug. 15, 2014, 2 pages.

Saltzman et al., "Prospective Controlled Trial of Star Total Ankle Replacement Versus Ankle Fusion: Initial Results," Foot & Ankle International, vol. 30, No. 7, Jul. 2009, pp. 579-596.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Scranton JR. et al., "Anatomic Variations in the First Ray: Part I. Anatomic Aspects Related to Bunion Surgery," Clinical Orthopaedics and Related Research, vol. 151, Sep. 1980, pp. 244-255.

Siddiqui et al. "Fixation of Metatarsal Fracture With Bone Plate in a Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

"Smith & Nephew scores a Hat-Trick with its entry into the high-growth hammer toe repair market," Smith & Nephew, Jul. 31, 2014, 2 pages.

Stableloc External Fixation System, Acumed, Product Overview, Effective date Sep. 2015, 4 pages.

Stahl et al., "Derotation of Post-Traumatic Femoral Deformities by Closed Intramedullary Sawing," Injury, vol. 37, No. 2, Feb. 2006, pp. 145-151, (Abstract Only).

Talbot et al.,"Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

Tricot et al., "3D-corrective osteotomy using surgical guides for posttraumatic distal humeral deformity," Acta Orthopaedica Belgica, vol. 78, No. 4, 2012, pp. 538-542.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fußchirurgie Das V-tek-System," ABW Wissenschaftsverlag GmbH, 2009, 11 pages, including English Abstract.

Weber et al., "A Simple System for Navigation of Bone Alignment Osteotomies of the Tibia," International Congress Series, vol. 1268, Jan. 2004, pp. 608-613, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

Yasuda et al., "Proximal Supination Osteotomy of the First Metatarsal for Hallux Valgus," Foot and Ankle International, vol. 36, No. 6, Jun. 2015, pp. 696-704.

Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.

Conti et al., "Effect of the Modified Lapidus Procedure on Pronation of the First Ray in Hallux Valgus," Foot & Ankle International, Feb. 1, 2020, published online: Oct. 16, 2019, 8 pages.

Conti et al., "Effect of the Modified Lapidus Procedure for Hallux Valgus on Foot Width," Foot & Ankle International, Feb. 1, 2020, published online: Oct. 30, 2019, 6 pages.

Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.

Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.

Hatch et al., "Triplane Hallux Abducto Valgus Classification," The Journal of Foot & Ankle Surgery, vol. 57, No. 5, Sep./Oct. 2018, published online: May 18, 2018, pp. 972-981.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Lopez et al., "Metatarsalgia: Assessment Algorithm and Decision Making," Foot and Ankle Clinics, vol. 24, No. 4, Dec. 2019, published online: Sep. 25, 2019, pp. 561-569.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Walker et al., "The Role of First Ray Insufficiency in the Development of Metatarsalgia," Foot and Ankle Clinics, vol. 24, No. 4, Dec. 2019, published online: Sep. 5, 2019, pp. 641-648.

Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.

Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.

Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.

Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.

Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.

"Accu-Cut Osteotomy Guide System," BioPro, Brochure, Oct. 2018, 2 pages.

(56) References Cited

OTHER PUBLICATIONS

"Acumed Osteotomiesystem Operationstechnik," Acumed, 2014, 19 pages (including 3 pages English translation).

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

Alvine et al., "Peg and Dowel Fusion of the Proximal Interphalangeal Joint," Foot & Ankle, vol. 1, No. 2, 1980, pp. 90-94.

Anderson et al., "Uncemented Star Total Ankle Prostheses," The Journal of Bone and Joint Surgery, vol. 86(1, Suppl 2), Sep. 2004, pp. 103-111, (Abstract Only).

Bednarz et al., "Modified Lapidus Procedure for the Treatment of Hypermobile Hallux Valgus," Foot & Ankle International, vol. 21, No. 10, Oct. 2000, pp. 816-821.

Blomer, "Knieendoprothetik—Herstellerische Probleme und technologische Entwicklungen," Orthopade, vol. 29, 2000, pp. 688-696, including English Abstract on p. 689.

Bouaicha et al., "Fixation of Maximal Shift Scarf Osteotomy with Inside-Out Plating: Technique Tip," Foot & Ankle International, vol. 32, No. 5, May 2011, pp. 567-569.

Carr et al., "Correctional Osteotomy for Metatarsus Primus Varus and Hallux Valgus," The Journal of Bone and Joint Surgery, vol. 50-A, No. 7, Oct. 1968, pp. 1353-1367.

Coetzee et al., "The Lapidus Procedure: A Prospective Cohort Outcome Study," Foot & Ankle International, vol. 25, No. 8, Aug. 2004, pp. 526-531.

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.

"Futura Forefoot Implant Arthroplasty Products," Tornier, Inc., 2008, 14 pages.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.

Garthwait, "Accu-Cut System Facilitates Enhanced Precision," Podiatry Today, vol. 18, No. 6, Jun. 2005, 6 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems für die Knieendoprothetik," Forschungsberichte, Technische Universitat Munchen, 165, 2002, 11 pages, including partial English Translation.

Gregg et al., "Plantar plate repair and Weil osteotomy for metatarsophalangeal joint instability," Foot and Ankle Surgery, vol. 13, 2007, pp. 116-121.

Grondal et al., "A Guide Plate for Accurate Positioning of First Metatarsophalangeal Joint during Fusion," Operative Orthopädie und Traumatologie, vol. 16, No. 2, 2004, pp. 167-178 (Abstract Only).

"Hat-Trick Lesser Toe Repair System," Smith & Nephew, Brochure, Aug. 2014, 12 pages.

"Hat-Trick Lesser Toe Repair System, Foot and Ankle Technique Guide, Metatarsal Shortening Osteotomy Surgical Technique," Smith & Nephew, 2014, 16 pages.

Hetherington et al., "Evaluation of surgical experience and the use of an osteotomy guide on the apical angle of an Austin osteotomy," The Foot, vol. 18, 2008, pp. 159-164.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.

"Hoffmann II Compact External Fixation System," Stryker, Brochure, Literature No. 5075-1-500, 2006, 12 pages.

"Hoffmann II Micro Lengthener," Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Mortier et al., "Axial Rotation of the First Metatarsal Head in a Normal Population and Hallux Valgus Patients," Orthopaedics and Traumatology: Surgery and Research, vol. 98, 2012, pp. 677-683.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

"Lag Screw Target Bow," Stryker Leibinger GmbH & Co. KG, Germany 2004, 8 pages.

Lapidus, "The Author's Bunion Operation From 1931 to 1959," Clinical Orthopaedics, vol. 16, 1960, pp. 119-135.

Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Magin, "Computernavigierter Gelenkersatz am Knie mit dem Orthopilot," Operative Orthopädie und Traumatologie, vol. 22, No. 1, 2010, pp. 63-80, including English Abstract on p. 64.

Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.

Michelangelo Bunion System, Surgical Technique, Instratek Incorporated, publication date unknown, 4 pages.

Mini Joint Distractor, Arthrex, retrieved Dec. 19, 2014, from the Internet: <http://www.arthrex.com/foot-ankle/mini-joint-distractor/products>, 2 pages.

(56) References Cited

OTHER PUBLICATIONS

MiniRail System, Small Bone Innovations, Surgical Technique, 2010, 24 pages.

Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect of Ankle Flexion Angle on Axial Alignment of Total Ankle Replacement," Foot and Ankle International, vol. 31, No. 12, Dec. 2010, pp. 1093-1098, (Abstract Only).

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Dayton et al., "The Extended Knee Hemilithotomy Position for Gastrocnemius Recession," The Journal of Foot and Ankle Surgery, vol. 49, 2010, pp. 214-216.

Wienke et al., "Bone Stimulation for Nonunions: What the Evidence Reveals," Podiatry Today, vol. 24, No. 9, Sep. 2011, pp. 52-57.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Dayton et al., "A User-Friendly Method of Pin Site Management for External Fixators," Foot and Ankle Specialist, Sep. 16, 2011, 4 pages.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Technique for Minimally Invasive Reduction of Calcaneal Fractures Using Small Bilateral External Fixation," The Journal of Foot and Ankle Surgery, Article in Press, 2014, 7 pages.

Dayton et al., "Clarification of the Anatomic Definition of the Bunion Deformity," The Journal of Foot and Ankle Surgery, vol. 53, 2014, pp. 160-163.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Dayton et al., "Principles of Management of Growth Plate Fractures in the Foot and Ankle," Clinics in Podiatric Medicine and Surgery, Pediatric Foot Deformities, Oct. 2013, 17 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Catanese et al., "Measuring Sesamoid Position in Hallux Valgus: When Is the Sesamoid Axial View Necessary," Foot and Ankle Specialist, 2014, 3 pages.

Dayton et al., "Comparison of Complications for Internal and External Fixation for Charcot Reconstruction: A Systematic Review," The Journal of Foot and Ankle Surgery, Article in Press, 2015, 4 pages.

Dayton et al., "A new triplanar paradigm for bunion management," Lower Extremity Review, Apr. 2015, 9 pages.

Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.

Dayton et al., "Complications of Metatarsal Suture Techniques for Bunion Correction: A Systematic Review of the Literature," The Journal of Foot and Ankle Surgery, Article in Press, 2015, 3 pages.

Decarbo et al., "The Weil Osteotomy: A Refresher," Techniques in Foot and Ankle Surgery, vol. 13, No. 4, Dec. 2014, pp. 191-198.

Decarbo et al., "Resurfacing Interpositional Arthroplasty for Degenerative Joint Diseas of the First Metatarsalphalangeal Joint," Podiatry Management, Jan. 2013, pp. 137-142.

Decarbo et al., "Locking Plates: Do They Prevent Complications?," Podiatry Today, Apr. 2014, 7 pages.

Easley et al., "Current Concepts Review: Hallux Valgus Part II: Operative Treatment," Foot and Ankle International, vol. 28, No. 6, Jun. 2007, pp. 748-758.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Easley et al., "What is the Best Treatment for Hallux Valgus?," Evidence-Based Orthopaedics—The Best Answers to Clinical Questions, Chapter 73, 2009, pp. 479-491.

Shurnas et al., "Proximal Metatarsal Opening Wedge Osteotomy," Operative Techniques in Foot and Ankle Surgery, Section I, Chapter 13, 2011, pp. 73-78.

Defendant Fusion Orthopedics LLC's Invalidity Contentions, No. CV-22-00490-PHX-SRB, US District Court for the District of Arizona, Aug. 27, 2022, 41 pages.

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.

Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.

Claim Chart for Fishco, "A Straightforward Guide to the Lapidus Bunionectomy," HMP Global (Sep. 6, 2013), Exhibit B2 of Defen-

(56)                     References Cited

OTHER PUBLICATIONS dant Fusion Orthopedics LLC's Invalidity Contentions, No. CV-22-00490-PHX-SRB, US District Court for the District of Arizona, Aug. 27, 2022, 67 pages.

Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.

"Anatomy of the Foot and Ankle," OrthoPaedia, Retrieved online from <https://orthopaedia.com/page/Anatomy-of-the-Foot-Ankle> on Feb. 21, 2022, 21 pages.

Farac et al., "Arthroscopy of the Great and Lesser Toes," Musculoskeletal Key, Retrieved online from <https://musculoskeletalkey.com/arthroscopy-of-the-great-and-lesser-toes/> on Feb. 18, 2022, dated Sep. 25, 2018, 7 pages.

AWH, "Turf Toe," Radsource, MRI Web Clinic, Retrieved online from <https://radsource.us/clinic-turf-toe/>, dated Jan. 2012, 20 pages.

"Integra Jarit Surgical Instruments," Integra, 2011, 916 pages.

* cited by examiner

MAKE INCISION — 602

CUT SOFT TISSUE USING CUTTING INSTRUMENT — 604

PREPARE BONE ENDS FOR FUSION — 606

REALIGN AT LEAST ONE BONE — 608

COMPRESS BONE ENDS — 610

FIXATE MOVED BONE POSITION — 612

MULTI-SIDED CUTTING INSTRUMENT FOR MOBILIZING SMALL BONES IN THE FOOT

CROSS-REFERENCE

This application claims the benefit of U.S. Provisional Patent Application No. 63/313,124, filed Feb. 23, 2022, the entire contents of which are incorporated herein by reference.

TECHNICAL FIELD

This disclosure relates to surgical cutting instruments and, more particularly, to multi-sided cutting instruments for releasing soft tissues between bones in the foot.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion.

Another type of bone deformity in the foot is metatarsus adductus. MTA is a deformity of the foot in which the metatarsals are angulated into adduction. MTA is typically characterized by a medial deviation of the metatarsals in the transverse plane. For example, MTA is often described as a structural deformity occurring at the Lisfranc joint (tarso-metatarsal joints), with the metatarsals being deviated medially with reference to the lesser tarsus.

In some cases, surgical intervention is needed to address hallux valgus and/or MTA deformities. Surgical intervention may involve realigning one or more bones of the foot, improving patient comfort and increasing patient mobility. A clinician may use a variety of different surgical instruments during a surgical procedure performed on the foot, including one or more cutting instruments to cut tissue and/or bone. Surgical instruments that can facilitate efficient, accurate, and reproducible clinical results are useful for practitioners performing bone realignment techniques.

SUMMARY

In general, this disclosure is directed to orthopedic cutting instruments and associated systems and techniques utilizing such cutting instruments. In some examples, an orthopedic cutting instrument according to the disclosure can be used to cut and release soft tissue, such as ligaments, tendons, and/or muscle, between bones during a surgical procedure. For example, during a bone realignment procedure, a joint space between adjacent bones may be surgically accessed. The cutting instrument can then be inserted into and/or across the joint space to cut soft tissue in and/or around the joint space. Cutting this soft tissue can release and mobilize a bone defining the joint space, increasing the range of motion over which the bone can be moved for realigning the bone during the surgical procedure.

In some implementations, the cutting instrument is configured with a handle graspable by a clinician performing the procedure and a cutting head operatively connected to the handle. The cutting head can have multiple different cutting surfaces, or cutting facets, arranged relative to each other to facilitate controlled cutting for the target surgical procedure. For example, the cutting head may be configured with a leading cutting surface and a pair of side cutting surfaces extending angularly away from the leading cutting surface. The leading cutting surface can define a straight cutting edge perpendicular to the longitudinal axis of the cutting instrument and the side cutting surfaces can define side cutting edges extending obliquely to the longitudinal axis of the cutting instrument. The leading cutting edge can be used to cut tissue as the cutting instrument is advanced axially into the joint space. The side cutting edges can be used to cut tissue as the cutting instrument is moved back and forth (e.g., medially and laterally; distally and proximally) within the joint space.

In some configurations, the linear cutting edge defined by the leading cutting surface is comparatively smaller than the maximum width of the cutting head measured between the side cutting edges. For example, the width of the cutting head may taper from a maximum width between the side cutting edges to a narrowed width defined by the leading cutting edge. At the same time, the leading cutting edge may define a minimum length, providing a cutting edge that is more than just a sharpened point. Configuring the cutting head with a comparatively small leading cutting edge that widens out via side cutting edges to define a larger cutting head width can be useful to help the clinician deliver controlled cutting via the instrument. The comparatively narrow leading cutting edge can allow the clinician to initiate axial advancement of the cutting head into the joint space and/or tissue to be cut. The subsequent widening of the cutting head can generate resistance to the axial advancement of the cutting head (e.g., as the comparatively wider portion of the cutting head encounters a wider section of tissue to be cut). This configuration can allow the clinician to effectively initiate a cut while helping to prevent the clinician from plunging the instrument too deeply into the joint space, e.g., which may otherwise cut tissue not intended to be cut during the surgical procedure.

An orthopedic cutting instrument according to disclosure can be used in any desired surgical procedure. In some configurations, the cutting instrument may find particular utility in releasing soft tissue in joint spaces of the foot prior to realigning one or more bones defining the joint space being released. The bones in the foot and corresponding joint spaces are small compared to many other larger bones and joint spaces in the body. This can make precision cutting in and around a joint space more delicate than when working in larger anatomical areas of the body.

In one example, an orthopedic cutting instrument is described that includes a handle and a cutting head. The handle has a length extending from a first end to a second end. The cutting head extends from the second end of the handle. According to the example, the cutting head includes a leading cutting surface, a first side cutting surface, and a second side cutting surface. The first side cutting surface extends angularly outwardly from the leading cutting surface on a first side of the cutting head. The second side cutting surface extends angularly outwardly from the leading cutting surface in a direction opposite the first side cutting surface on a second side of the cutting head.

In another example, a method of preparing a joint is described. The method involves inserting a cutting head into a joint space defined between a first bone and a second bone and moving the cutting head within the joint space to cut soft tissue between the first bone and the second bone. The example specifies that the cutting head includes a leading cutting surface, a first side cutting surface, and a second side cutting surface. The first side cutting surface extends angularly outwardly from the leading cutting surface on a first side of the cutting head. The second side cutting surface extends angularly outwardly from the leading cutting surface in a direction opposite the first side cutting surface on a second side of the cutting head.

The details of one or more examples are set forth in the accompanying drawings and the description below. Other features, objects, and advantages will be apparent from the description and drawings, and from the claims.

DETAILED DESCRIPTION

Figures 1A, 1B:
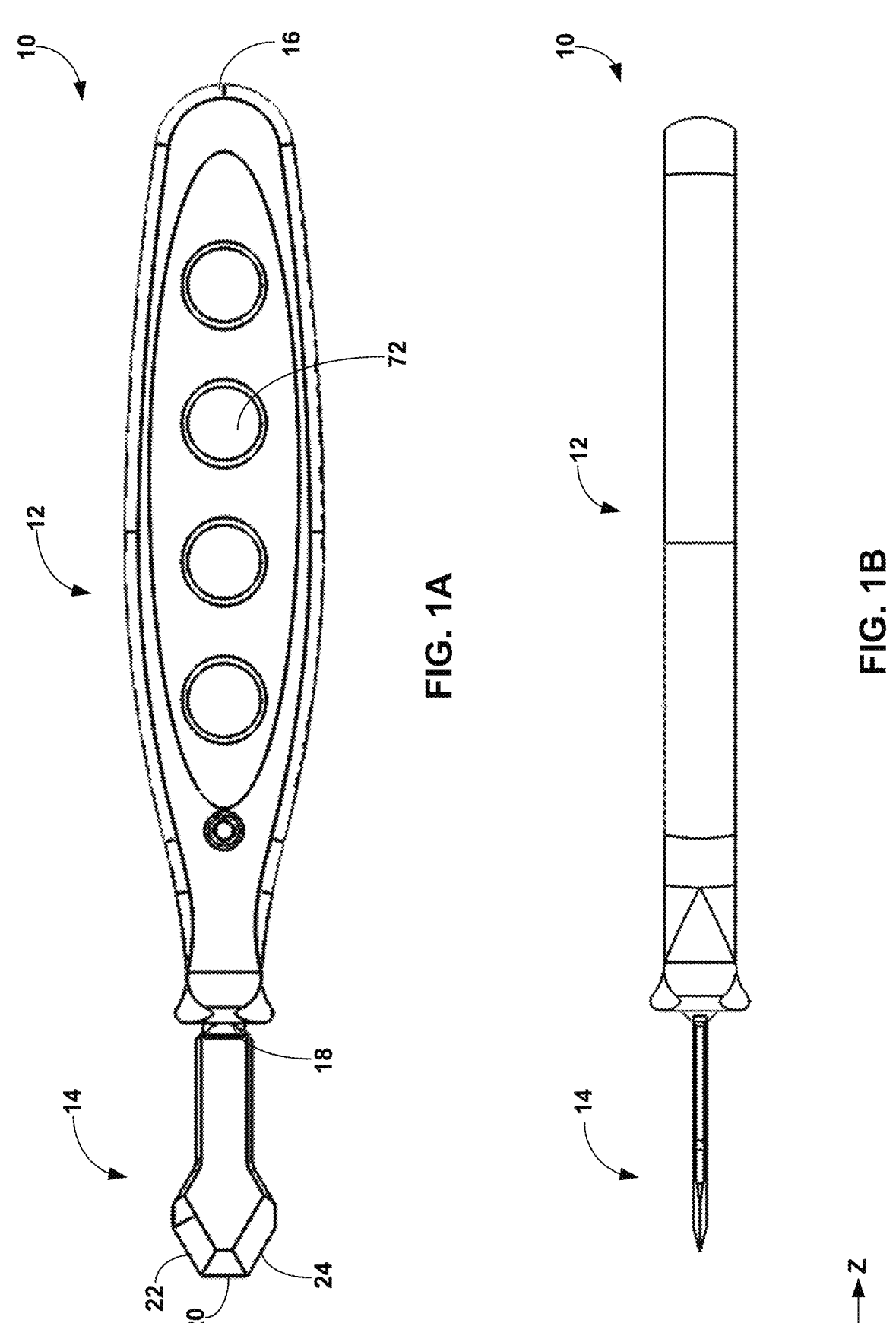
FIGS. 1A and 1B are top and side views, respectively, of an example orthopedic cutting instrument according to the disclosure.

This disclosure generally relates to orthopedic cutting instruments and associated systems (e.g., kits) and techniques incorporating one or more such cutting instruments. In some examples, a cutting instrument according to the disclosure can be used to cut soft tissue connecting a bone to an adjacent bone, helping to mobilize the bone for a subsequent repositioning step. For example, the cutting instrument may be used to cut soft tissue during a metatarsal realignment and fusion procedure. While the instrument may find particular utility cutting soft tissue, in practice, the clinician can use the instrument to cut and/or shape bone, scrape cartilage, and/or preform any other procedures desired by the clinician using the instrument without departing from the scope of the disclosure.

In exemplary applications, the devices, systems, and techniques can be used during a surgical procedure performed on one or more bones, such as a bone alignment, osteotomy, fusion procedure, fracture repair, and/or other procedures where one or more bones are to be set in a desired position. Such a procedure can be performed, for example, on bones (e.g., adjacent bones separated by a joint or different portions of a single bone) in the foot or hand, where bones are relatively small compared to bones in other parts of the human anatomy. In one example, a procedure utilizing devices and/or techniques of the disclosure can be performed to correct an alignment between a metatarsal (e.g. a first metatarsal) and a cuneiform (e.g., a medial cuneiform), such as a bunion correction. An example of such a procedure is a lapidus procedure. In another example, the devices, systems, and/or techniques can be utilized when modifying a position of one portion of a bone relative to another portion of the same bone. An example of such a procedure is an osteotomy procedure (e.g., metatarsal osteotomy procedure) in which the bone is cut into at least two different bones and one portion (e.g., a distal portion) is realigned relative to another bone portion (e.g., a proximal portion) of the same bone.

Preparation and fusion of one or more TMT joints may be performed according to the disclosure for a variety of clinical reasons and indications. Preparation and fusion of a TMT joint may be performed to treat metatarsus adductus, hallux valgus, arthritis, and/or other bone and/or joint conditions.

Metatarsus adductus is a deformity of the foot characterized by a transverse plane deformity where the metatarsals are adducted at the Lisfranc joint. The extent of a metatarsus adductus deformity can be characterized by a metatarsus adductus angle. The metatarsus adductus angle can be defined as the angle between the longitudinal axis of the second metatarsal (representing the longitudinal axis of the metatarsus) and the longitudinal axis of the lesser tarsus. The measurement of the longitudinal axis of the lesser tarsus can be characterized by a line perpendicular to the transverse axis of the lesser tarsus using the lateral joint of the fourth metatarsal with the cuboid as a reference.

Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux adductus angle, the angle between the long axes of the first metatarsal and proximal phalanx in the transverse plane. An increase in the hallux adductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced, e.g., laterally relative to the first metatarsophalangeal joint, resulting in subluxation of the joints between the sesamoid bones and the head of the first metatarsal. This can increase the pressure between the medial sesamoid and the *crista* of the first metatarsal head.

While techniques and devices are generally described herein in connection with the first metatarsal and medial cuneiform of the foot, the techniques and devices may be used on other adjacent bones (e.g., separated from each other by a joint) and/or adjacent bone portions (e.g., portions of the same bone separated from each other by a fracture or osteotomy). In various examples, the devices, systems, and/or techniques of the disclosure may be utilized on comparatively small bones in the foot such as a metatarsal (e.g., first, second, third, fourth, or fifth metatarsal), a cuneiform (e.g., medial, intermediate, lateral), a cuboid, a phalanx (e.g., proximal, intermediate, distal), and/or combinations thereof. The bones may be separated from each other by a tarsometatarsal ("TMT") joint, a metatarsophalangeal ("MTP") joint, or other joint. Accordingly, reference to a first metatarsal and medial cuneiform herein may be replaced with other bone pairs as described herein.

The anatomy of the foot and example techniques utilizing a cutting instrument according to the disclosure will be described in greater detail with respect to FIGS. 4-8. However, an example orthopedic cutting instrument according to the disclosure will first be described with respect to FIGS. 1-3.

FIGS. 1A and 1B (collectively referred to as "FIG. 1") are top and side views, respectively, of an example orthopedic cutting instrument 10 according to the disclosure. Cutting instrument 10 includes a handle 12 and a cutting head 14 operatively connected to the handle. For example, in the illustrated configuration, handle 12 has a major length extending from a first end 16 to a second end 18. Cutting head 14 is connected to and extends from the second end 18 of handle 12. In various implementations, handle 12 and cutting head 14 may be fabricated as a unitary body (e.g., cut or cast as a single piece of material) or may be fabricated as separate components that are joined together to form a combined structure the does not separate during use.

As will be described in greater detail below, cutting head 14 can be configured with multiple different cutting surfaces (which may also be referred to as cutting facets) controllably arranged relative to each other. Cutting head 14 can include leading and side cutting surfaces that are interconnected together to form an overall cutting profile for the cutting head. In use, a clinician can advance a cutting head 14 in multiple different directions, utilizing different cutting surfaces of the cutting head depending on the specific direction in which the clinician is advancing the cutting head. This can allow the clinician to accurately and efficiently cut tissue or other structure at a target location during a surgical procedure.

While cutting instrument 10 can be used for any desired surgical procedure, in some configurations, the cutting instrument is configured (e.g., sized and shaped) to facilitate cutting within a joint space between opposed bones of the foot. For example, cutting head 14 of cutting instrument 10 may be configured to be inserted into a tarsometatarsal joint space between a metatarsal and an opposed bone (a cuneiform, a cuboid) and/or in an intermetatarsal space between adjacent metatarsals. The clinician may insert cutting head 14 of cutting instrument 10 into one or more of these target joint spaces when preparing a metatarsal (or portion thereof) for subsequent realignment. For example, the clinician may insert cutting head 14 of cutting instrument 10 into the target joint space(s) to cut soft tissue (e.g., muscles, tendons, ligaments, and/or facia) within the joint space. Such soft tissue may be connectively attached to the bone (e.g., metatarsal) intended to be realigned. Cutting the soft tissue using cutting instrument 10 can mobilize the bone for subsequent realignment. After realignment and other associated surgical steps, the realigned bone may be permanently fixated in a moved position using a fixation device to promote fusion of the realigned bone across the joint space.

With reference to FIG. 1A, cutting head 14 is illustrated as including a leading cutting surface 20, a first side cutting surface 22, and a second side cutting surface 24. Leading cutting surface 20 may define the distal-most cutting surface of cutting head 14 (with the first end 16 of handle 12 defining the proximal-most portion of cutting instrument 10). First side cutting surface 22 and second side cutting surface 24 can be separated from each other in the widthwise direction across cutting head 14, e.g., where the width of the cutting head is perpendicular to the length of cutting instrument 10 and the material thickness of the cutting head. First side cutting surface 22 can extend angularly outwardly from leading cutting surface 20 on a first widthwise side of the cutting head. Second side cutting surface 24 can extend angularly outwardly from leading cutting surface 20 in a direction opposite first side cutting surface 22 on a second widthwise side of cutting head 14.

Figure 1C:
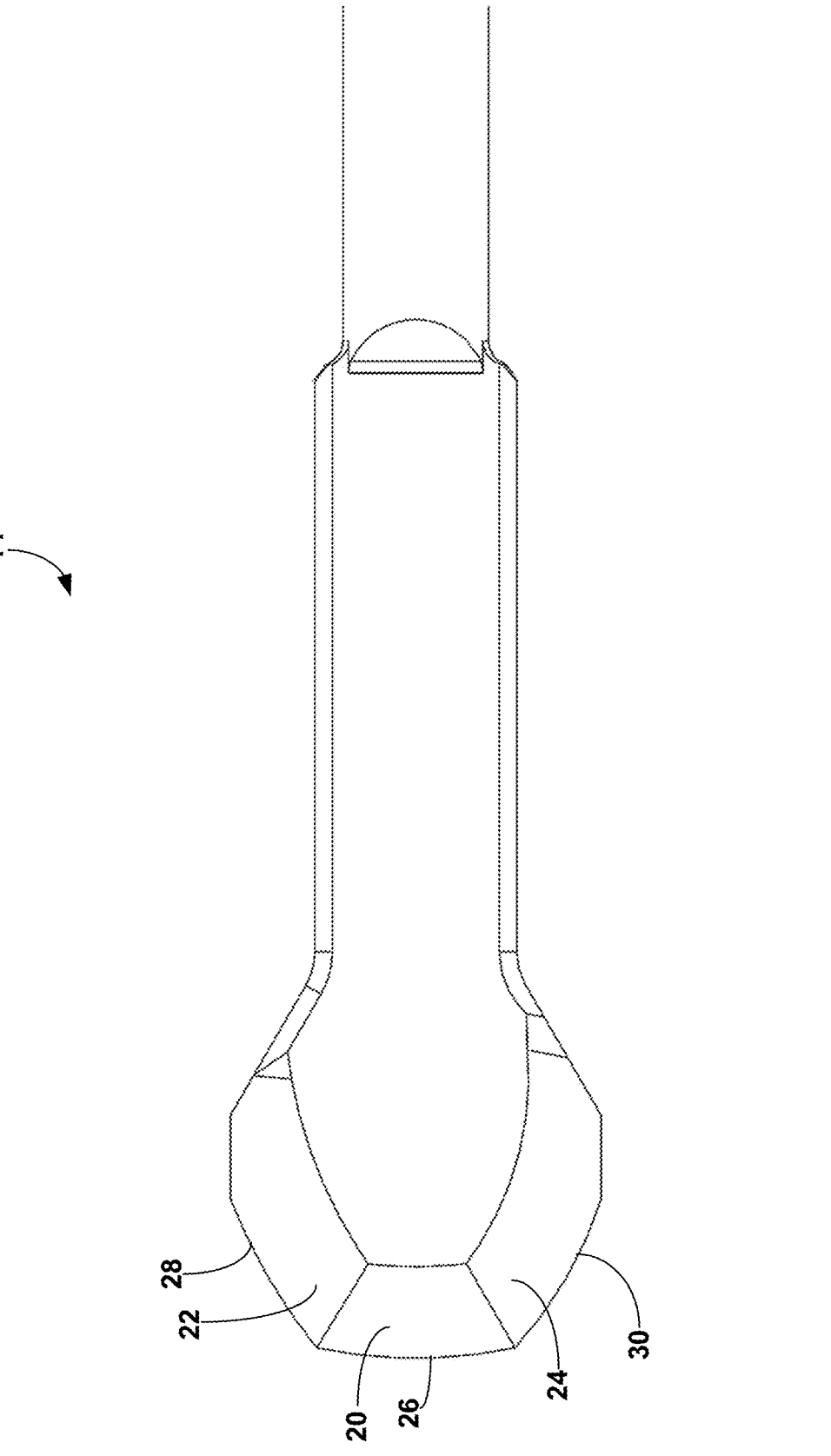
FIGS. 1C and 1D are top views of example configurations of the cutting head of the example cutting instrument of FIGS. 1A and 1B where one or more the cutting edges of cutting head define a curvature across the length of the edge.
Figure 1D:
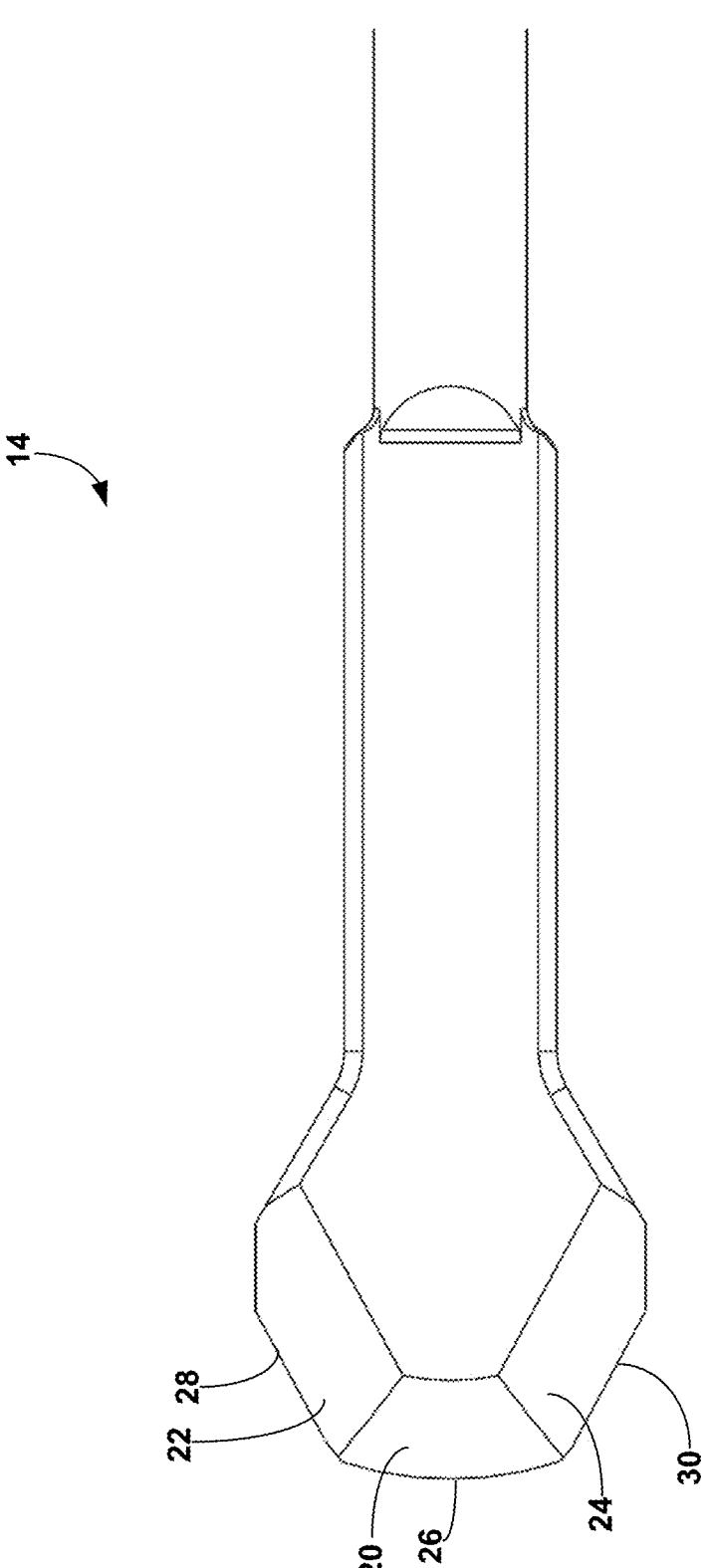
Figure 2:
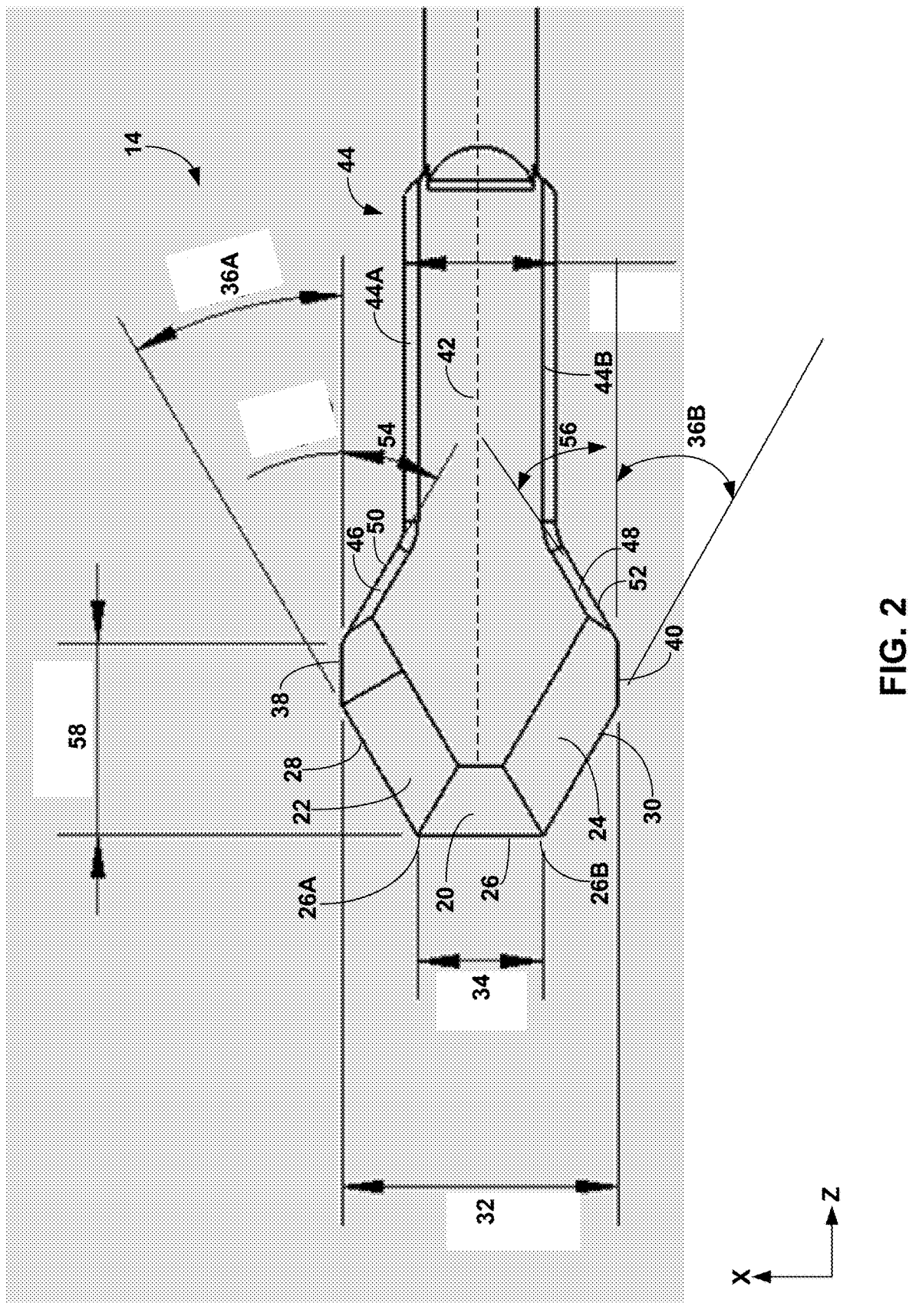
FIG. 2 is an enlarged view of the cutting head from FIG. 1 illustrating an example configuration of features for the cutting head.

FIG. 2 is an enlarged view of cutting head 14 from FIG. 1 illustrating an example configuration of features for the cutting head. FIG. 2 illustrates leading cutting surface 20 defining a leading cutting edge 26, first side cutting surface 22 defining a first side cutting edge 28, and second side cutting surface 24 defining a second side cutting edge 30. First side cutting surface 22, and first side cutting edge 28 defined thereby, is illustrated as extending angularly away from leading cutting surface 20, and leading cutting edge 26 defined thereby, in the widthwise direction (e.g., positive X-direction indicated on FIG. 2). Second side cutting surface 24, and second side cutting edge 30 defined thereby, is illustrated as extending angularly away from leading cutting surface 20, and leading cutting edge 26 defined thereby, in a generally opposite widthwise direction (e.g., negative X-direction indicated on FIG. 2). As a result, the overall width of cutting head 14 in the configuration of FIG. 2 enlarges moving from leading cutting edge 26 of the cutting head proximally along the portion of the cutting head defined by first and second side cutting edges 28, 30.

Configuring cutting head 14 with a comparatively narrow leading cutting surface 20 (and leading cutting edge 26 defined thereby) trailed by a comparatively wider region of the cutting head defined by the first and second side cutting surfaces 22, 24 (and side cutting edges 28, 30 defined thereby) can be useful to facilitate controlled penetration of the cutting head by the clinician during use. The comparatively narrow leading cutting surface 20 allows the clinician to apply concentrated force to a comparatively small leading cutting edge 26 for introducing the cutting instrument into a joint space and/or applying cutting force to tissue to be cut. The comparatively wider trailing region of cutting head 14 expands out the region of cut created by the cutting head. This can increase the cutting surface area of cutting head 14, increasing the amount of tissue cut while at the same time providing increased resistance against the cutting head. This can help prevent the clinician from inadvertently plunging cutting head 14 too deep into a joint space during the procedure, which can otherwise cut muscle, tendons, and/or other tissue not desired to be cut during the procedure.

In some implementations, cutting head 14 defines a maximum width 32 at a location between first side cutting surface 22 and second side cutting surface 24 that is rearward (proximal of) leading cutting surface 20. This maximum width 32 of cutting head 14 can be compared to the length 34 of leading cutting edge 26, e.g., the linear cutting edge extending widthwise at the distal tip of cutting head 14. The length 34 of leading cutting edge 26 can be set less than the maximum width 32 of cutting head 14, thereby configuring cutting head 14 with a comparatively narrow distal cutting tip that expands widthwise in a proximal direction.

While the specific dimensions of cutting head 14 can vary depending on the intended application, in some examples, leading cutting edge 26 defines a length 34 ranging from 1 mm to 15 mm, such as from 2 mm to 10 mm, or from 3 mm to 7 mm. For example, leading cutting edge 26 may define a length 34 of approximately 5 mm (e.g., ±10 percent). In addition, the maximum width 32 of cutting head 14 between first and second side cutting surfaces 22, 24 may range from 5 mm to 25 mm, such as from 7 mm to 20 mm, or from 9 mm to 13 mm. For example, the maximum width 32 of cutting head 14 may be approximately 11 mm (e.g., ±10 percent).

Depending on the relative widthwise dimensions of cutting head 14 at different locations along the length of the cutting head, a ratio of the length 34 of the leading cutting edge 26 divided by the maximum width 32 of the cutting head may range from 0.25 to 0.75, such as from 0.35 to 0.5. For example, the ratio of the length 34 of the leading cutting edge 26 divided by the maximum width 32 of the cutting head may be less than 0.5, such as less than 0.45, or less than 0.4.

In the configuration of FIG. 2, first side cutting surface 22 extends angularly outwardly from leading cutting surface 20, and second side cutting surface 24 extends angularly outwardly from leading cutting surface 20 in a different direction than the first side cutting surface. For example, leading cutting edge 26 defined by leading cutting surface 20 may extend from a first end 26A to a second end 26B. First side cutting edge 28 may intersect first end 26A of leading cutting edge 26 and extend outwardly therefrom. Second side cutting edge 30 may intersect second end 26B of leading cutting edge 26 and extend outwardly therefrom. The angle at which first and second side cutting surfaces 22, 24 extend away from leading cutting surface 20 may be defined by angle of intersection between the leading cutting surface and first and second side surfaces, respectively.

As discussed above, leading cutting surface 20 may terminate at the distal-most end in leading cutting edge 26, which may be referred to as a linear cutting edge due to the straight or non-curved linear shape of the edge (when so configured). In addition, first side cutting surface 22 may terminate in an outermost edge, forming first side cutting edge 28, which may also be referred to as a first angled side edge. Second side cutting surface 24 may also terminate in an outermost edge, forming second side cutting edge 30, which may also be referred to as a second angled side edge. First side cutting edge 28 can intersect leading cutting edge 26 to define a first intersection angle 36A. Second side cutting edge 30 can intersect leading cutting edge 26 to define a second intersection angle 36B. In some examples, one or more cutting edges cutting head 14 may define a curvature (e.g., a concave or convex curvature).

In some configurations, such as that illustrated in FIG. 2, first intersection angle 36A and second intersection angle 36B may have a same value to provide a symmetrical enlargement of cutting head 14 extending away from leading cutting edge 26. In other configurations, first intersection angle 36A may be different than second intersection angle 36B (e.g., larger or smaller) to provide an asymmetrical enlargement of cutting head 14. In various examples, first intersection angle 36A and/or second intersection angle 36B may range from 10 degrees to 75 degrees, such as from 15 degrees to 45 degrees, or from 25 degrees to 35 degrees. For example, first intersection angle 36A and/or second intersection angle 36B may be approximately 30 degrees (e.g., ±10%).

First side cutting surface 22 and/or second side cutting surface 24 may extend angularly outwardly from leading cutting surface 22 along the entire length of cutting head 14. When so configured, the overall width of cutting head 14 may continuously enlarge from the distal-most end of the cutting head defined by leading cutting edge 26 to the proximal-most end of the cutting head. In other configurations, first side cutting surface 22 and/or second side cutting surface 24 may extend angularly outwardly from leading cutting surface 20 for a portion of the length of cutting head 14 before changing direction to extend parallel to the length and/or back towards a longitudinal center of the cutting head. In these latter configurations, cutting head 14 may define a comparatively narrow distal region, a comparatively narrow proximal region, and a comparatively wider intermediate region between the distal and proximal regions.

In the example of FIG. 2, first side cutting surface 22 defines first side cutting edge 28 extending angularly outwardly at first intersection angle 36A and further includes an adjacent first straight side edge 38 proximal to the angled first side cutting edge. In addition, second side cutting surface 24 defines second side cutting edge 30 extending angularly outwardly at second intersection angle 36B and further includes an adjacent second straight side edge 40 proximal to the angled second side cutting edge.

In the illustrated arrangement, first straight side edge 38 and second straight side edge 40 are each parallel to each other and also parallel to a longitudinal axis 42 defined by cutting head 14. In some configurations, first straight side edge 38 is longer than first side cutting edge 28 and/or second straight side edge 40 is longer than second side cutting edge 30. In other configurations, such as that illustrated, first straight side edge 38 is shorter than the first side cutting edge 28 and/or second straight side edge 40 is shorter than second side cutting edge 30. For example, first straight side edge 38 and second straight side edge 40 may each have a length (measured along the face of the edge) less than 75% of the overall length of first side cutting edge 28 and second side cutting edge 30, respectively, such as less than 50% of the overall length, less than 40% of the overall length, or less than 25% of the overall length.

Independent of whether cutting head 14 is configured with first straight side edge 38 and/or second straight side edge 40, the cutting head may include one or more recessed surfaces narrowing the overall with of the cutting head. In the configuration of FIG. 2, cutting head 14 narrows from a region of maximum width 32 down to a shank 44 positioned proximally of leading cutting surface 20, first side cutting surface 22, and second side cutting surface 24. The transition between first side cutting surface 22 and second side cutting surface 24 and the proximal shank 44 (along with one or more intermediate regions, such as first straight side surface 38 and second straight side surface 40, when included) may be abrupt (e.g., a 90° angular in cut) or may tapered at a more gradual angle. In either case, angled recessed surfaces may be defined where cutting head 14 tapers down to shank 44.

In the example of FIG. 2, cutting head 14 defines a first recessed surface 46 extending angularly inwardly from first side cutting surface 22 to shank 44. Cutting head 14 also defines a second recessed surface 48 extending angularly inwardly from second side cutting surface 24 to shank 44. For example, cutting head 14 may define a first recessed surface edge 50 extending between first side cutting edge 28 (with first straight side edge 38 interposed therebetween, when so configured) and a first edge 44A bounding shank 44. Cutting head 14 may also define a second recessed surface edge 52 extending between second side cutting edge 30 (with second straight side edge 40 interposed therebetween, when so configured) and a second edge 44B bounding shank 44.

First recessed surface 46 can define a first recess intersection angle 54 with first side cutting surface 22. Similarly, second recessed surface 48 can define a second recess intersection angle 56 with second side cutting surface 24. First recess intersection angle 54 and second recess intersection angle 56 may each range from 5° to 90°, such as from 10° to 75°, from 15° to 40°, or from 25° to 35°. For example, first recess intersection angle 54 and second recess intersection angle 56 may each be approximately 30° (e.g., ±10%).

The specific dimensions of cutting instrument 10, including one or more cutting surfaces of cutting head 14, can vary depending on the desired application. In some implementations, first side cutting surface 22 and second side cutting surface 24 are sized to facilitate cutting within comparatively small joint spaces. First side cutting surface 22 and second side cutting surface 24 may each be characterized by a longitudinal length 58 extending parallel to the longitudinal axis 42 of cutting head 14. In some configurations, length 58 is greater than 3 mm, such as greater than 5 mm and/or less than 25 mm, such as less than 15 mm, or less than 10 mm. For example, length 58 may range from 5 mm to 15 mm, such as from 6 mm to 9 mm. The length 58 of first side cutting surface 22 may be the same as or different than the length 58 of second side cutting surface 22.

In some configurations, cutting head 14 defines an overall length (e.g., from the distal end of leading cutting surface 20 to the second end 18 of handle 12 as illustrated on FIG. 1) ranging from 10 mm to 100 mm, such as from 15 mm to 45 mm. Handle 12 can have any desired length between first end 16 and second end 18 although, in some examples, may exhibit a length ranging from 50 mm to 200 mm, such as from 100 mm to 150 mm.

In general, features of cutting head 14 described as cutting surfaces may define regions of the cutting head having a reduced thickness compared to a remainder of the cutting head. The reduced thickness of the cutting surfaces may facilitate cutting as cutting head 14 is placed in contact with material to be cut. Each cutting surface may be formed by tapering the thickness of cutting head 14 in the region of the cutting surface (e.g., from a region of comparatively greater thickness toward the center of the cutting head to a region of comparatively lesser thickness at the outermost edge of the cutting surface). For example, with reference to FIG. 1B, the thickness of cutting head 14 in the Y-direction indicated on the figure can be tapered over the region of each cutting surface defined by the cutting head (e.g., including leading cutting surface 20, first side cutting surface 22, and second side cutting surface 24). The size and configuration of each cutting surface may vary, as described herein. In some implementations, such as those illustrated, leading cutting surface 20 defines a trapezoid having a long base at the distal most-end of cutting head 14, a short base proximally located, a first leg joining the long base to the short base, and a second leg joining the long base to the short base.

In the example of FIGS. 1A, 1B, and 2, the cutting edges of cutting head 14 are illustrated as being straight or non-curved. In particular, leading cutting edge 26 of leading cutting surface 20, first side cutting edge 28 of first side cutting surface 22, and second side cutting edge 30 of second side cutting surface 24 are each illustrated as being straight edges that do not have any curvature along the length of the edges. In other configurations, one or more of the cutting edges of cutting head 14 may define a curvature across the length of the edge.

For example, FIGS. 1C and 1D are top views of other example configurations of cutting head 14 of cutting instrument 10 where one or more the cutting edges of cutting head 14 define a curvature across the length of the edge. In particular, FIG. 1C illustrates an example configuration of cutting head 14 in which leading cutting edge 26 of leading cutting surface 20, first side cutting edge 28 of first side cutting surface 22, and second side cutting edge 30 of second side cutting surface 24 each define a curvature across the length of the respective edges. FIG. 1D illustrates an example configuration of cutting head 14 in which leading cutting edge 26 of leading cutting surface 20 defines a curvature across the length of the edge while first side cutting edge 28 of first side cutting surface 22 and second side cutting edge 30 of second side cutting surface 24 are each illustrated as being straight edges that do not have any curvature across the length of the edge. When configured with a curved edge, the edge may define a convex radius of curvature in which a portion of the edge extends outwardly at an intermediate portion of the edge along its length relate to portions of the edge at lengthwise ends of the edge.

Figures 3A, 3B:
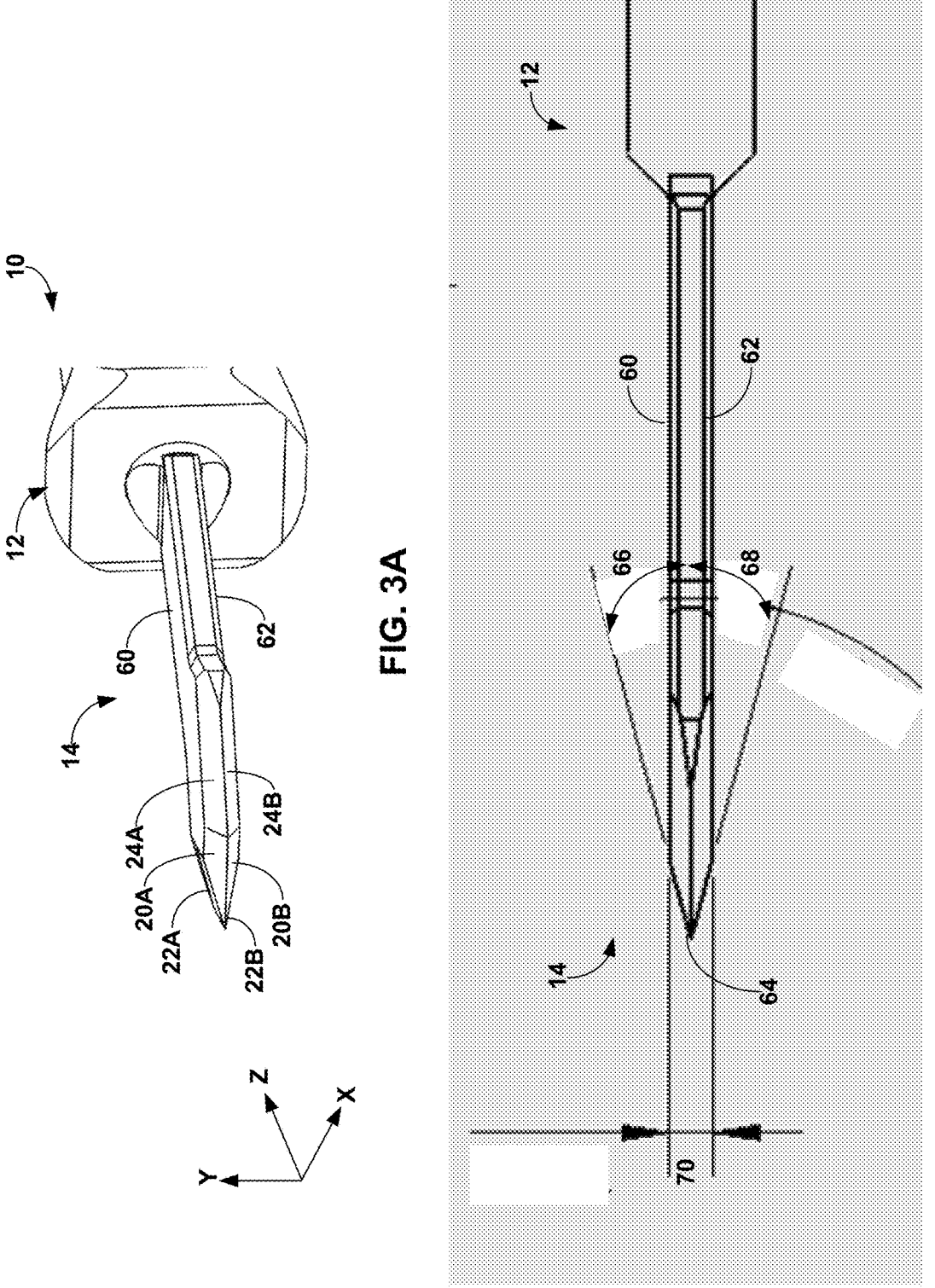
FIGS. 3A and 3B are a front perspective view and a side view, respectively, of the cutting instrument of FIG. 1 showing example taper profiles of the cutting head.

FIGS. 3A and 3B (collectively referred to as FIG. 3) are a front perspective view and a side view, respectively, of cutting instrument 10 showing example taper profiles of cutting head 14. As shown in FIG. 3, the cutting surfaces of cutting head 14 are tapered across the thickness of the material defining the cutting head, thereby forming planes with comparatively sharp edges (e.g., apexes) for cutting tissue.

In some implementations, cutting head 14 defines cutting surfaces on a single side of the cutting head. For example, a first planar surface 60 can be defined by the length and width of cutting head 14 (e.g., in the X-Z plane indicated on FIG. 3A) on one side of the cutting head, and a second planar surface 62 can be defined by the length and width of cutting head 14 on the opposite side of the cutting head. Cutting surfaces defined by cutting head 14 can extend at an angle across the thickness of the cutting head (e.g., in the Y-direction indicated on FIG. 3A) toward the opposite planar surface.

In some examples, cutting head 14 defines cutting surfaces extending in a single direction across the thickness of the cutting head (e.g., from first plane 60 toward second plane 62 in the negative Y-direction), without having cutting surfaces extend in the opposite direction (e.g., from second plane 62 toward first plane 60 in the positive Y-direction). In these configurations, cutting surfaces may be defined on the first planar side 60 of cutting head 14, and the second planar side 62 of the cutting head may be devoid of cutting surfaces. This configuration may be referred to as a single-sided taper configuration.

In other configurations, however, cutting head 14 may define cutting surfaces on both sides of the cutting head. For example, cutting head 14 may include a first set of cutting surfaces tapered in a first direction across the thickness of the cutting head (e.g., from first plane 60 toward second plane 62 in the negative Y-direction) and a second set of cutting surfaces taped in a second direction across the thickness of the cutting head (e.g., from second plane 62 toward first plane 60 in the positive Y-direction). The two sets of cutting surfaces may intersect each other at a location between first plane 60 and second plane 62, e.g., at a location that is substantially centered across the thickness of the cutting head. For example, the two sets of cutting surfaces may intersect each other to define an intersection apex 64. This configuration may be referred to as a dual-sided taper configuration.

When configured with cutting surfaces on both sides of cutting head 14, the two sides of the cutting head may or may not have mirrored arrangements of cutting surfaces. For example, example configurations of cutting surfaces for a single side of cutting head 14 were described above with respect to FIG. 2. The opposite side of cutting head 14 may be configured with an identical set of cutting surfaces to those provided on the first side of the cutting head. This can provide a mirrored (e.g., symmetrical) arrangement in which the cutting surfaces on both sides of the cutting head have the same size, shape, and/or arrangement, albeit tapering in opposite directions from each other. The edges of the cutting surfaces on the two sides of cutting head 14 can intersect each other across the and thickness of the cutting head. In other configurations, cutting head 14 may have cutting surfaces on both sides of the cutting head that have a different size, shape, and/or arrangement from each other, providing an asymmetrical arrangement of cutting surfaces.

Cutting head 14 in the example of FIG. 3 is illustrated as having cutting surfaces on both sides of the cutting head that are symmetrically arranged. For example, with reference to FIG. 3A, cutting head 14 is illustrated as having a first leading cutting surface 20A on the first planar side 60 of the cutting head and a second leading cutting surface 20B on the second planar side 62 of the cutting head. Cutting head 14 also is illustrated as having a first side cutting surface 22A on the first planar side 60 of the cutting head and a first side cutting surface 22B on the second planar side 62 of the cutting. Cutting head 14 is further illustrated as having a second side cutting surface 24A on the first planar side 60 of the cutting head and a second side cutting surface 24B on the second planar side of the cutting head. Opposed pairs of cutting surfaces intersect each other across the thickness of the cutting head to form cutting edges (e.g., a leading cutting edge, a first side cutting edge, and a second side cutting edge). In some invitations, opposed pairs of cutting surfaces intersect each other each other at a midline across the thickness of the cutting.

The specific angle at which each cutting surface of cutting head 14 tapers towards an outermost edge can vary, e.g., based on the size and configuration of the cutting head. With reference to FIG. 3B, cutting head 14 can define a taper angle 66, which is the angle at which a cutting surface tapers across the thickness of the cutting head. In some examples, taper angle 66 may range from 5 degrees to 45 degrees, such as from 5 degrees to 25 degrees, or from 10 degrees to 20 degrees. When configured with cutting surfaces on both sides of cutting head 14 to provide a first taper angle 66 and a second taper angle 68, the two taper angles may be the same as or different than each other. Further, while all cutting surfaces on a single planar side of cutting head 14 may taper at the same taper angle, in other configurations, different cutting surfaces on a single side of cutting head 14 may taper at different angles relative to each other. In some implementations, the overall thickness 70 of cutting head 14 between first planar surface 60 and second 62 may range from 0.5 mm to 10, such as from 0.75 mm to 5 mm, from 1 mm to 2.5 mm, or from 1.25 mm to 1.75 mm.

In general, cutting instrument 10, including handle 12 and cutting head 14, can be formed of any desired material or combinations of materials. Typically, cutting head 14 will be fabricated of metal to form a sharp cutting surface, such as steel (e.g., stainless steel), titanium, or the like, although may be formed of ceramic or other sharpenable materials. Handle 12 may be formed of a variety of materials, including one or more metals and/or polymeric materials.

In some configurations, handle 12 and cutting head 14 are formed as a unitary structure (e.g., via casting, milling) defined by a single type of material. In other configurations, handle 12 and cutting head 14 may be formed as separate structures joined together to couple the cutting head to the handle for subsequent use. In some such configurations, handle 12 may be formed of a different material (e.g., a polymeric material) then cutting head 14 (which may be formed of metal material), e.g., for increased grip ability and/or comfort and holding. For example, handle 12 may define a receiving cavity at second and 18, and an end of cutting head 14 opposite leading cutting surface 20 can be inserted into the receiving cavity to interconnect the handling cutting head. Fixation means (e.g., adhesive, screws, bolts, welding) may be used to permanently affix the cutting head to the handle. In other configurations, cutting head 14 may be detachably attached to handle 12 to allow the handle to be used with different interchangeable cutting heads (e.g., each having the same configuration or having different configurations from each other).

Handle 12 may generally be configured to be gripped manually by the hand of a clinician using cutting instrument 10. Handle 12 may have an enlarged cross-sectional size (e.g., width, thickness) relative to cutting head 14 to provide a larger surface for grasping. In some configurations, handle 12 includes surface texturing 72, such as knobs, ribs, knurls, and/or other features that facilitate gripping of the handle without slippage. While handle 12 may generally be designed to be gripped manually by the hand of the clinician, in other configurations, handle 12 may be designed to be inserted into a powered hand instrument that can drive movement of cutting head 14 via the handle.

In the illustrated arrangements, handle 12 is illustrated as extending co-linearly with cutting head 14. That is, the longitudinal axis defined by handle 12 is illustrated as extending co-linearly with the longitudinal axis 42 defined by cutting head 14. In other configurations, handle 12 (the entire handle or portion thereof) may be offset from and/or angled relative to the longitudinal axis 42 defined by cutting head 14.

In configurations where handle 12 and cutting head 14 are formed as a unitary body and there is not an otherwise distinguishing transition between the handling cutting head, handle 12 may be deemed to have an arbitrary second end 18 between the handle and cutting head 14 where the handle transitions into the cutting head without distinguishing size or shape change between the handle and the cutting head.

As briefly discussed above, cutting instrument 10 can be used during a variety of different procedures, including as part of a bone alignment procedure. In some examples, cutting instrument 10 is utilized during a procedure in which one or more bones of the foot are realigned. To further understand such example techniques, the anatomy of the foot will be described with respect to FIGS. 4A and 4B. A bone misalignment in the foot may be caused by metatarsus adductus, hallux valgus (bunion), and/or other condition. The condition may present with a misalignment of one or more bones in the foot.

Figure 4B:
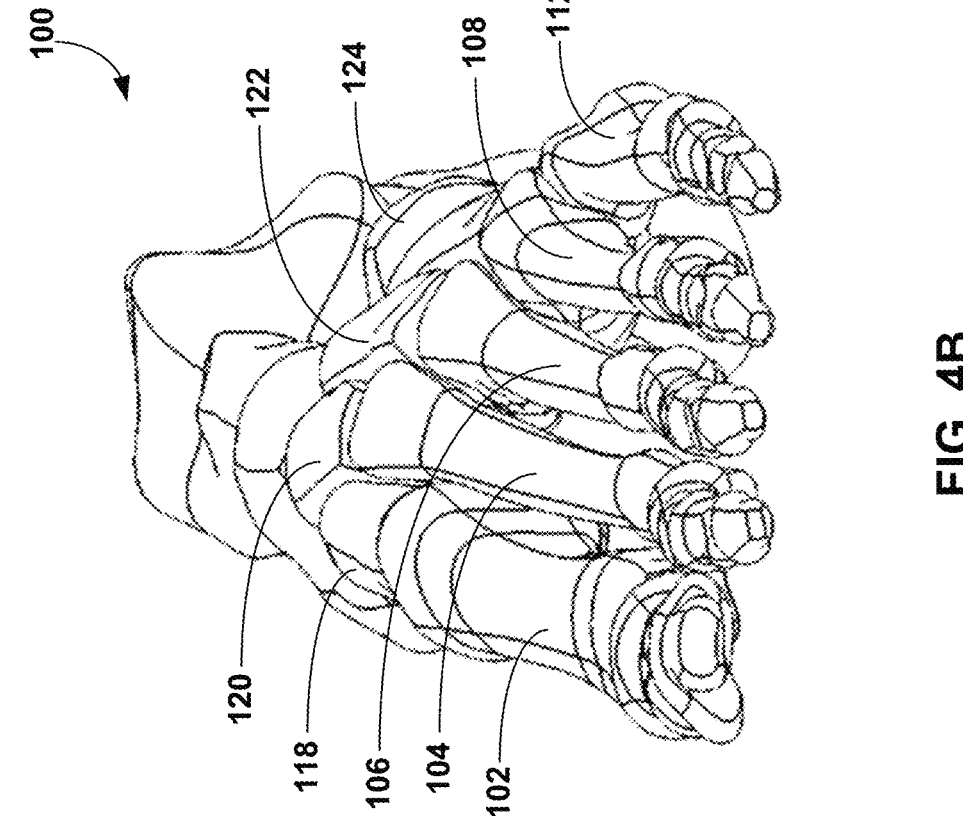
FIGS. 4A and 4B are top and front views, respectively, of a foot showing example normal metatarsal alignment positions.
Figure 4A:
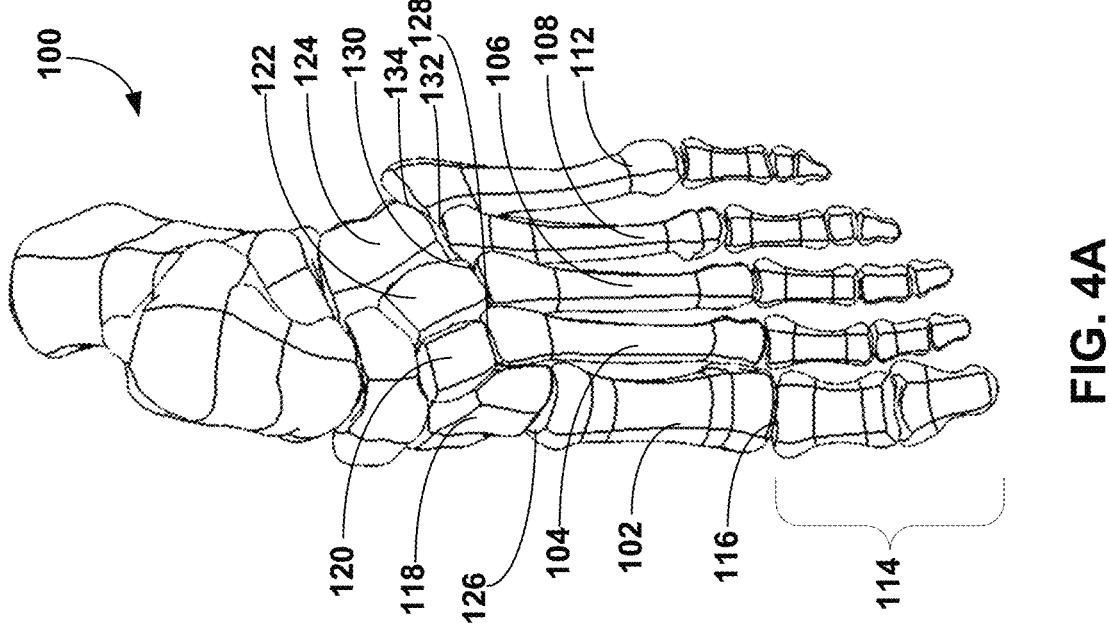

FIGS. 4A and 4B are top and front views, respectively, of a foot 100 showing normal metatarsal alignment positions. Foot 100 is composed of multiple bones including a first metatarsal 102, a second metatarsal 104, a third metatarsal 106, a fourth metatarsal 108, and a fifth metatarsal 112. First metatarsal 102 is on a medial-most side of the foot while fifth metatarsal 112 is on a lateral-most side of the foot. The metatarsals are connected distally to phalanges 114 and, more particularly, each to a respective proximal phalanx. The joint 116 between a metatarsal and a corresponding opposed proximal phalanx is referred to as a metatarsophalangeal ("MTP") joint. The first MTP joint is labeled as joint 116 in FIG. 1A, although second, third, fourth, and fifth MTP joints are also illustrated in series adjacent to the first MTP joint.

The first metatarsal 102 is connected proximally to a medial cuneiform 118, while the second metatarsal 104 is connected proximally to an intermediate cuneiform 120, and the third metatarsal 106 is connected proximally to lateral cuneiform 122. The fourth and fifth metatarsals 108, 112 are connected proximally to the cuboid bone 124. The joint between a metatarsal and opposed bone (cuneiform, cuboid) is referred to as the tarsometatarsal ("TMT") joint. FIG. 4A designates a first TMT joint 126, a second TMT joint 128, a third TMT joint 130, a fourth TMT joint 132, and a fifth TMT joint 134. The angle between adjacent metatarsals is referred to as the intermetatarsal angle ("IMA").

In the example of FIGS. 4A and 4B, foot 100 is illustrated as having generally normally aligned metatarsals. Normal metatarsal alignment may be characterized, among other attributes, by a low intermetatarsal angle (e.g., 9 degrees or less, such as 5 degrees or less) between the first metatarsal and the second metatarsal. In addition, the lesser metatarsals may be generally parallel to a longitudinal axis bisecting the foot proximally to distally.

Figure 5:
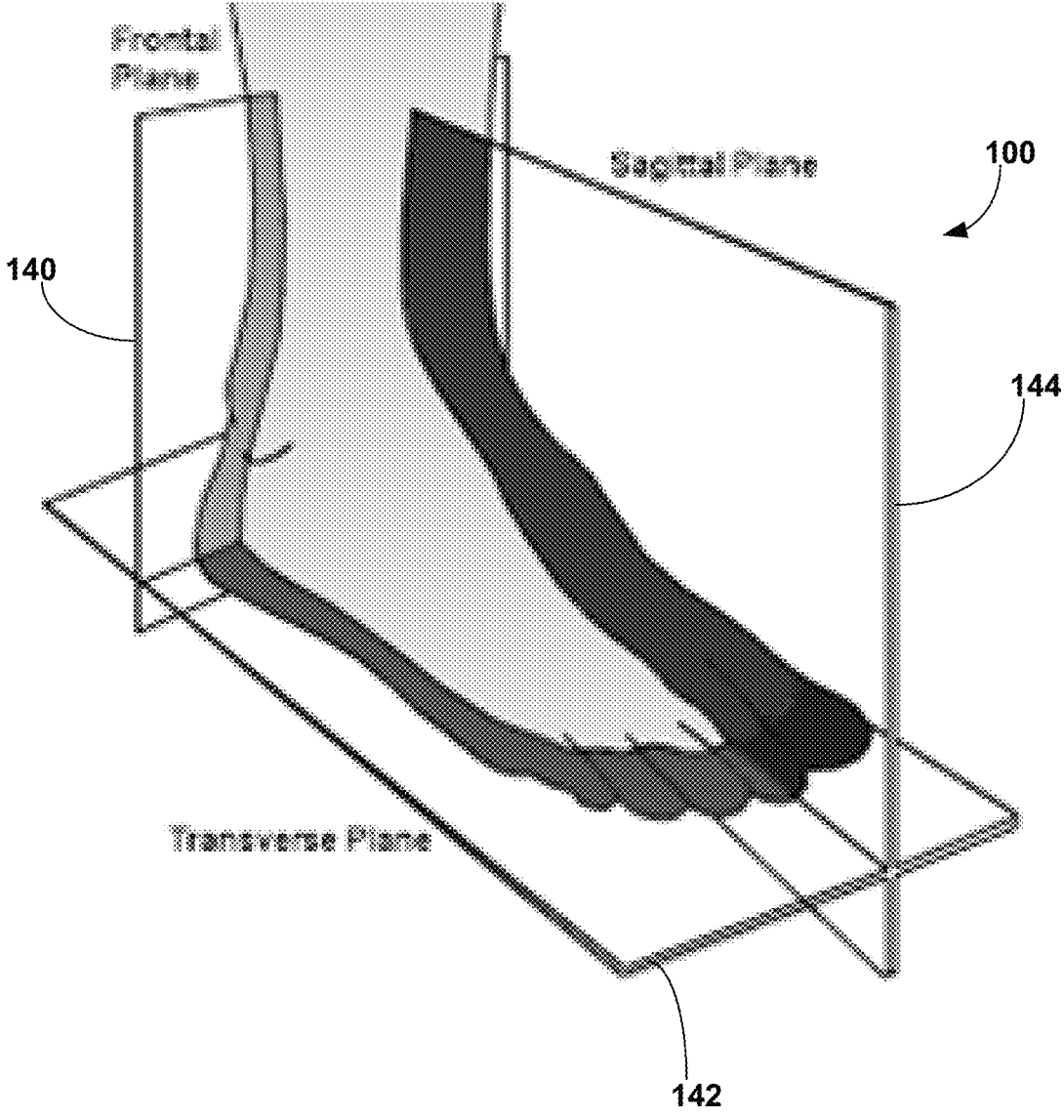
FIG. 5 illustrates the different anatomical planes of the foot.

FIG. 5 illustrates the different anatomical planes of foot 100, including frontal plane 140, transverse plane 142, and sagittal plane 144. The frontal plane 140, which is also known as the coronal plane, is generally considered any vertical plane that divides the body into anterior and posterior sections. On foot 100, the frontal plane 140 is a plane that extends vertically and is perpendicular to an axis extending proximally to distally along the length of the foot. The transverse plane 142, which is also known as the horizontal plane, axial plane, or transaxial plane, is considered any plane that divides the body into superior and inferior parts. On foot 100, the transverse plane 142 is a plane that extends horizontally and is perpendicular to an axis extending dorsally to plantarly (top to bottom) across the foot. Further, the sagittal plane 144 is a plane parallel to the sagittal suture which divides the body into right and left halves. On foot 100, the sagittal plane 144 is a plane that extends vertically and intersects an axis extending proximally to distally along the length of the foot. For patients afflicted with certain bone misalignments, one or more of metatarsals may be deviated medially in the transverse plane (e.g., in addition to or in lieu of being rotated in the frontal plane and/or being deviated in the sagittal plane relative to clinically defined normal anatomical alignment for a standard patient population).

Figure 6:
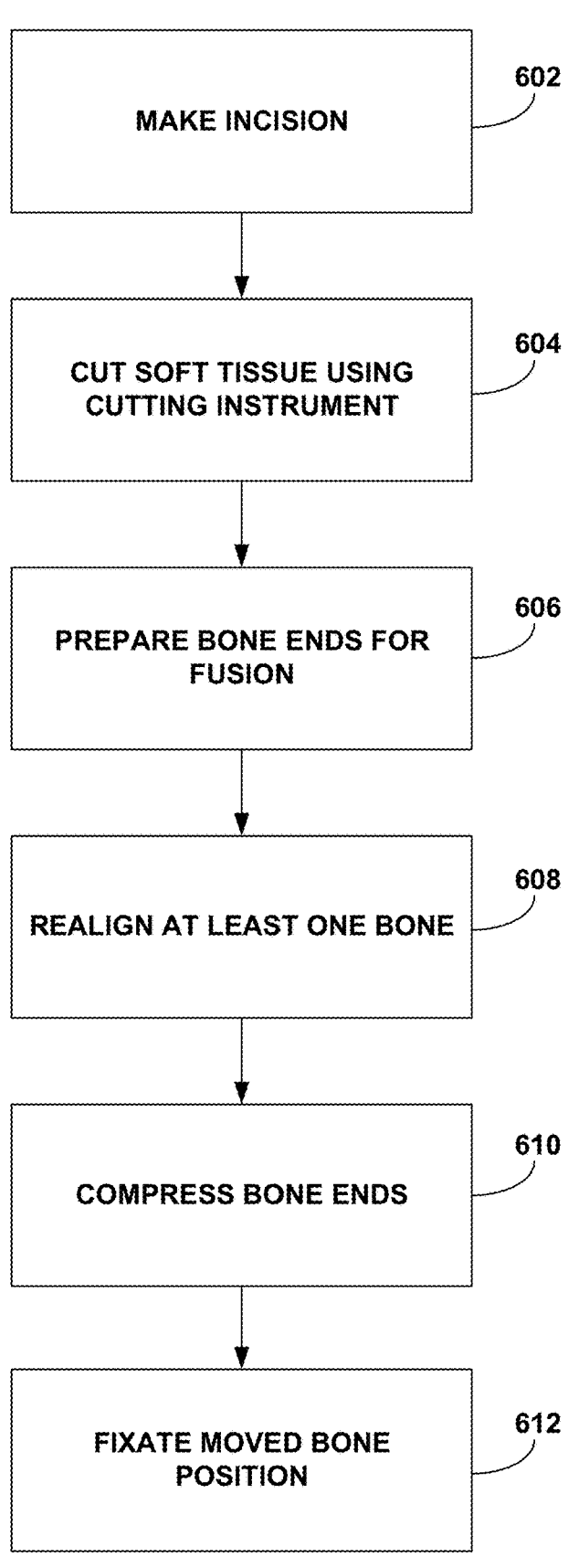
FIG. 6 is a flow diagram of an example bone realignment technique that can be performed utilizing a cutting instrument according to the disclosure.

FIG. 6 is a flow diagram of an example bone realignment technique that can be performed utilizing a cutting instrument 10 according to the disclosure. As will be described, in some examples of the technique of FIG. 6, cutting instrument 10 may be utilized to cut soft tissue to help mobilize a bone for subsequent bone realignment. In the example technique, an end of the bone being realigned and an end of an opposed bone across a tarsometatarsal joint may each be prepared and a fixation device installed across to the joint to promote fusion of the realigned bone across the joint. In other implementations, such as in an osteotomy procedure where a single bone is cut into two portions, one portion of the bone (e.g., a distal portion) may be realigned relative to the other portion (e.g., a proximal portion).

Example cutting steps utilizing cutting instrument 10 that can be performed will be described with reference to FIGS. 7 and 8. Additional details on example surgical techniques, including example instrumentation that can be used during the techniques, can be found in U.S. Pat. No. 9,622,805, issued Apr. 18, 2017 and entitled "BONE POSITIONING AND PREPARING GUIDE SYSTEMS AND METHODS," US Patent Publication No. 2020/0015856, published Jan. 16, 2020 and entitled "COMPRESSOR-DISTRACTOR FOR ANGULARLY REALIGNING BONE PORTIONS," and US Patent Publication No. 2021/0361330, published Nov. 25, 2021 and entitled "DEVICES AND TECHNIQUES FOR TREATING METATARSUS ADDUCTUS," the entire contents of each of which are incorporated herein by reference.

The example technique of FIG. 6 includes making an incision through the skin of the patient to surgically access a joint space (602). The incision can be made through the skin, such as on a dorsal side of the foot, a medial side of the foot, on a dorsal-medial side of the foot, on a lateral side of the foot, or yet other location in the foot. The incision can be made to provide surgical access to one or more of the first TMT joint 126, the second TMT joint 128, the third TMT joint 130, the fourth TMT joint 132, and the fifth TMT joint 134. Additionally or alternatively, the incision may be made to access one or more other joints such as a MTP joint and/or an intermetatarsal joint space between adjacent metatarsals. To surgically access a joint, the patient may be placed in a supine position on the operating room table and general anesthesia or monitored anesthesia care administered. Hemostasis can be obtained by applying thigh tourniquet or mid-calf tourniquet. In some examples, imaging of the foot can be used to assist the clinician in ascertaining the location of target joint about which incision can be centered when subsequently cutting through skin.

After surgically accessing one or more target joints, the technique of FIG. 6 involves cutting tissue in and/or around the one or more joints using cutting instrument 10 (604). For example, cutting instrument 10 can be inserted into a surgically-accessed joint space to cut soft tissue in the joint space to help release and mobilize a bone for subsequent repositioning. FIGS. 7A-7E illustrate example tissue cutting steps that can performed using cutting instrument 10 to release first metatarsal 102 for subsequent realignment.

Figure 7A:
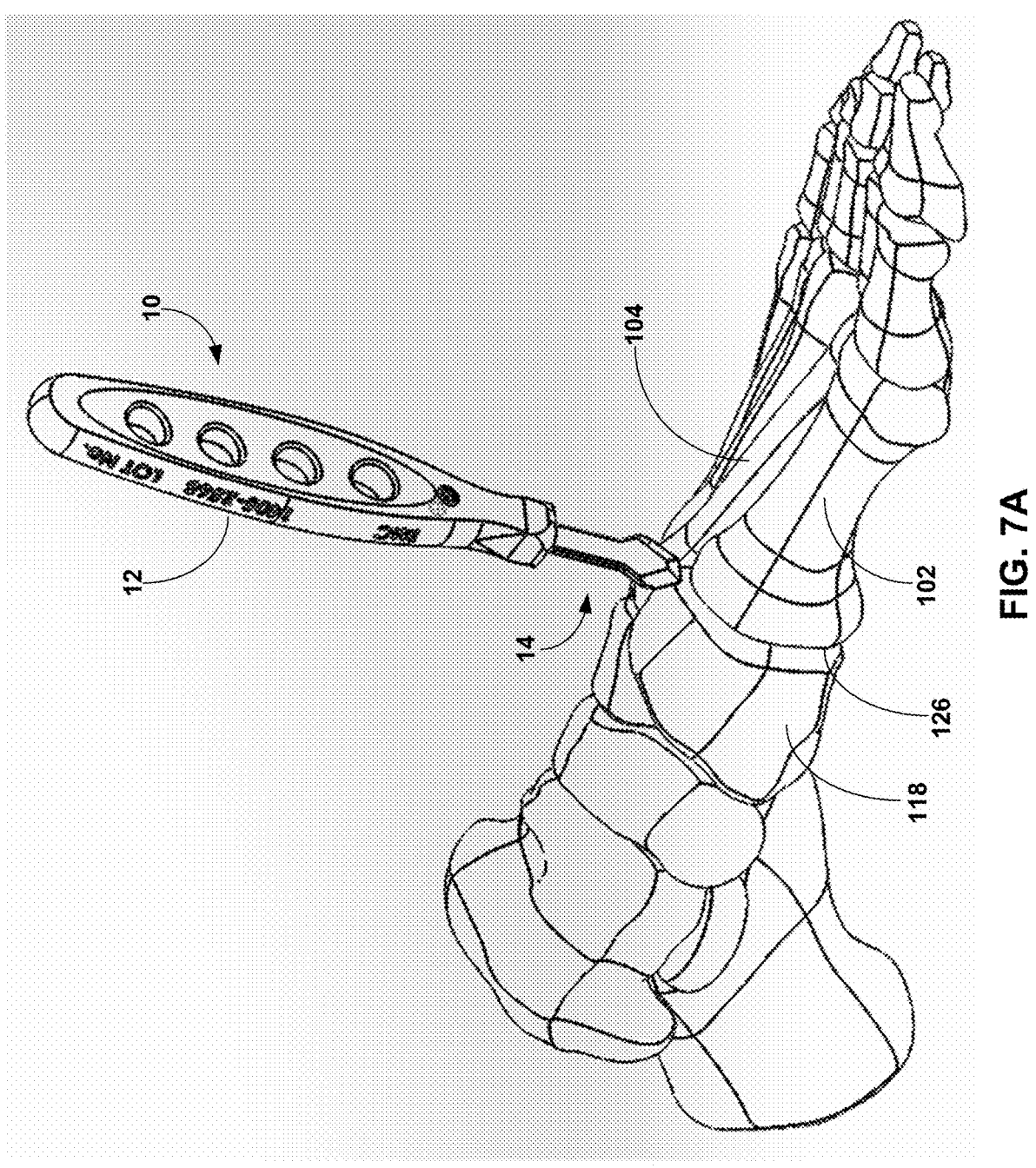
FIGS. 7A-7E illustrate example tissue cutting steps that can performed using a cutting instrument according to the disclosure.

With reference to FIG. 7A, an example cutting step using cutting instrument 10 is illustrated in which cutting head 14 of cutting instrument 10 is inserted into a tarsometatarsal joint space 126. Leading cutting surface 20 (FIG. 2) of cutting head 14 can be advanced downwardly (plantarly) into the tarsometatarsal joint space. The clinician can sweep cutting instrument 10 medially and laterally (e.g., forward and backward) within the joint space to cut tissue using the first and second side cutting surfaces defined by cutting head 14.

Figure 7B:
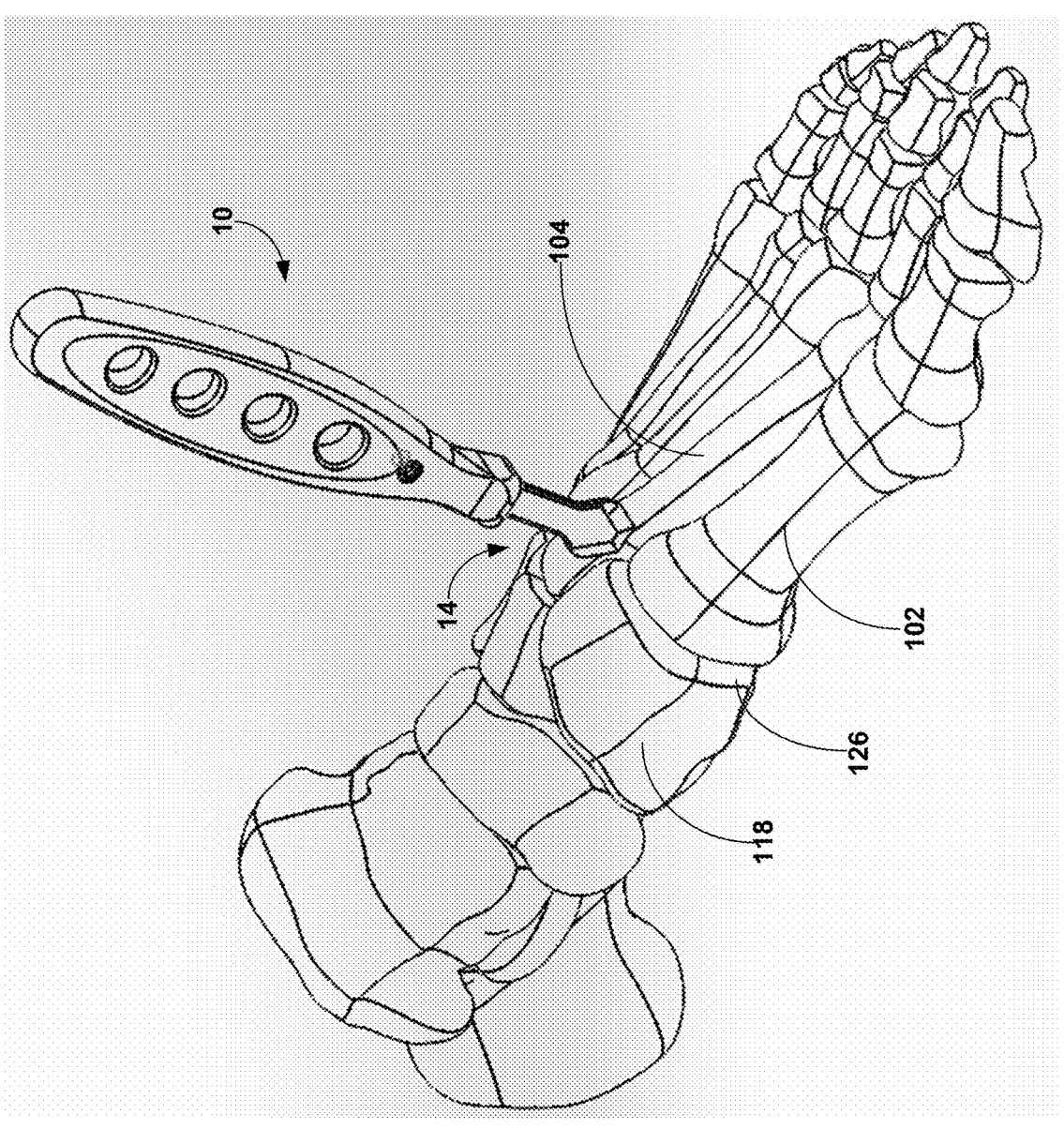

Before or after inserting cutting instrument 10 into tarsometatarsal joint space 126, the clinician may insert cutting head 14 of cutting instrument 10 into an intermetatarsal space between first metatarsal 102 and second metatarsal 104, as illustrated in FIG. 7B. The clinician can advance the leading cutting surface 20 of cutting head 14 plantarly into the intermetatarsal space between first metatarsal 102 and second metatarsal 104. The clinician may introduce cutting head 14 at the proximal base of first metatarsal 102 and sweep the instrument in a distal direction (down toward the distal end of the intermetatarsal space away from the intermediate cuneiform). Additionally or alternatively, the clinician may introduce cutting head 14 in the intermetatarsal space at a location distal to the proximal head of first metatarsal 102 and sweep the cutting instrument proximally up the intermetatarsal space. The clinician may also sweep cutting head 14 proximally and distally (e.g., backward and forward) within the intermetatarsal space. In either case, first side cutting surface 22 and/or second side surface 24 may cut tissue within the joint space.

In some applications, the clinician inserts cutting head 14 to an initial depth in the joint space and/or multiple joint spaces to initially open the joint spaces and subsequently advances a cutting head 14 deeper into the one or more joint spaces. For example, the clinician may initially insert cutting head 14 into tarsometatarsal joint space 126 (e.g., as illustrated in FIG. 7A) and subsequently insert cutting head 14 into the intermetatarsal joint space (e.g., as illustrated in FIG. 7B). The clinician may thereafter advance cutting head 14 deeper (farther plantarly) in the tarsometatarsal joint space 126 and/or the intermetatarsal space.

Figure 7C:
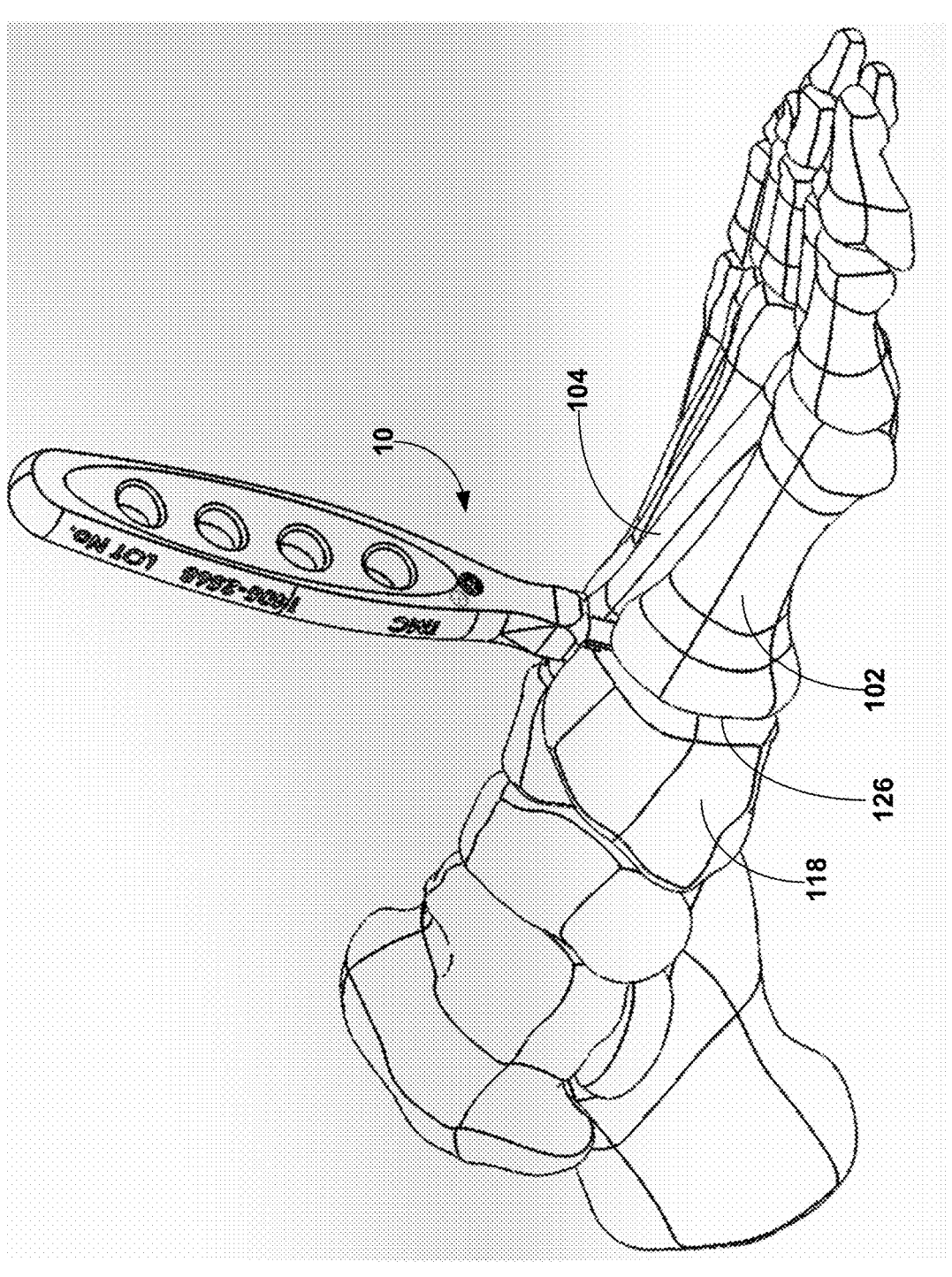
Figure 7D:
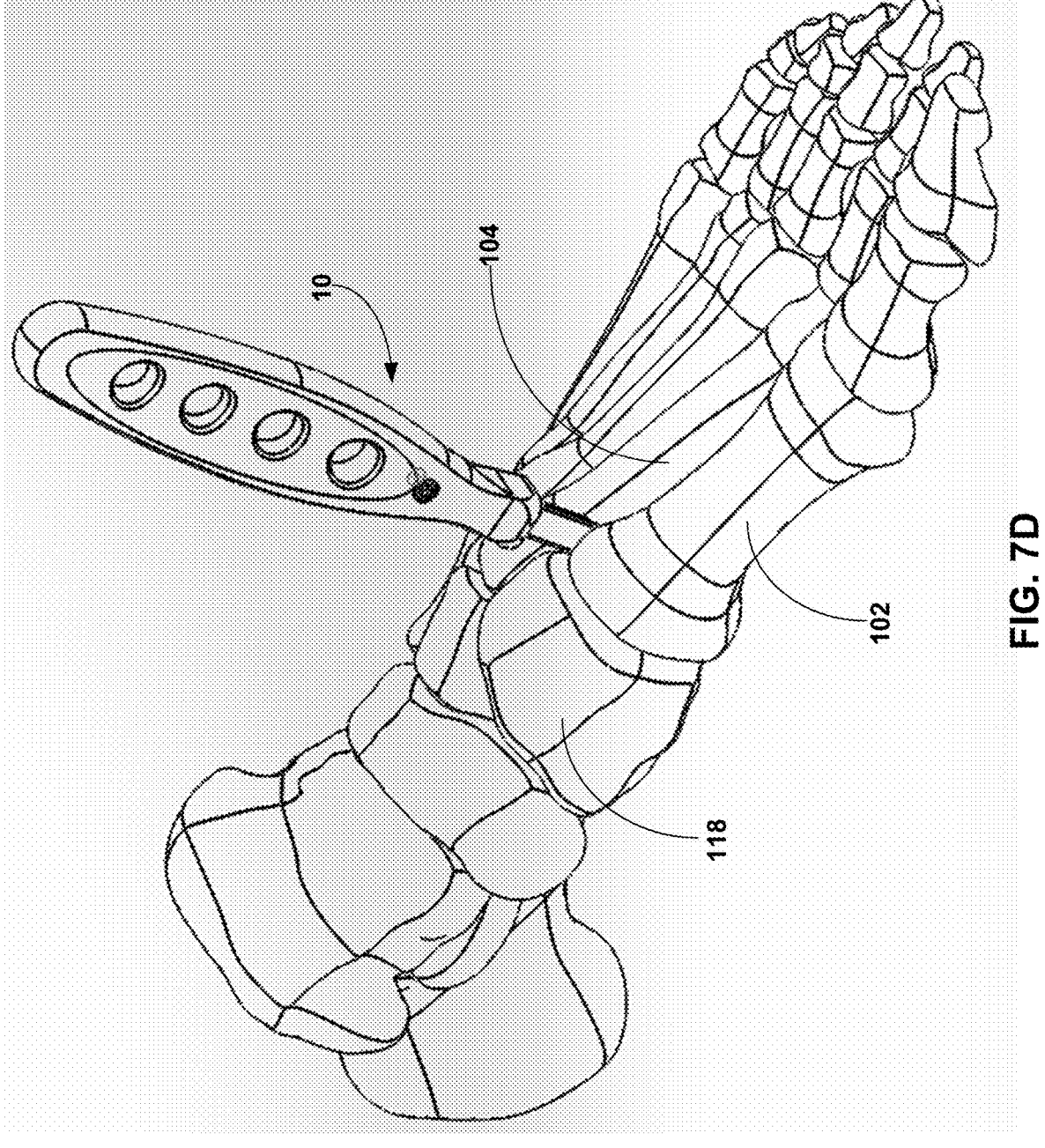

For example, FIGS. 7C and 7D illustrate cutting head 14 advanced deeper into the tarsometatarsal joint space 126 and intermetatarsal joint space, respectively. The clinician can advance the leading cutting surface 20 of cutting head 14 to a desired depth within one or both joint spaces. In some applications, the clinician reciprocates cutting head 14 up and down, cutting tissue with both leading cutting surface 20 (when advancing downwardly) and first and second recessed cutting surfaces 46, 48 (when retracting upwardly). The clinician can also sweep cutting head 14 side to side within one or both joint spaces at a desired depth, causing first side cutting surface 22 and/or second side surface 24 to cut tissue within the joint space.

Figure 7E:
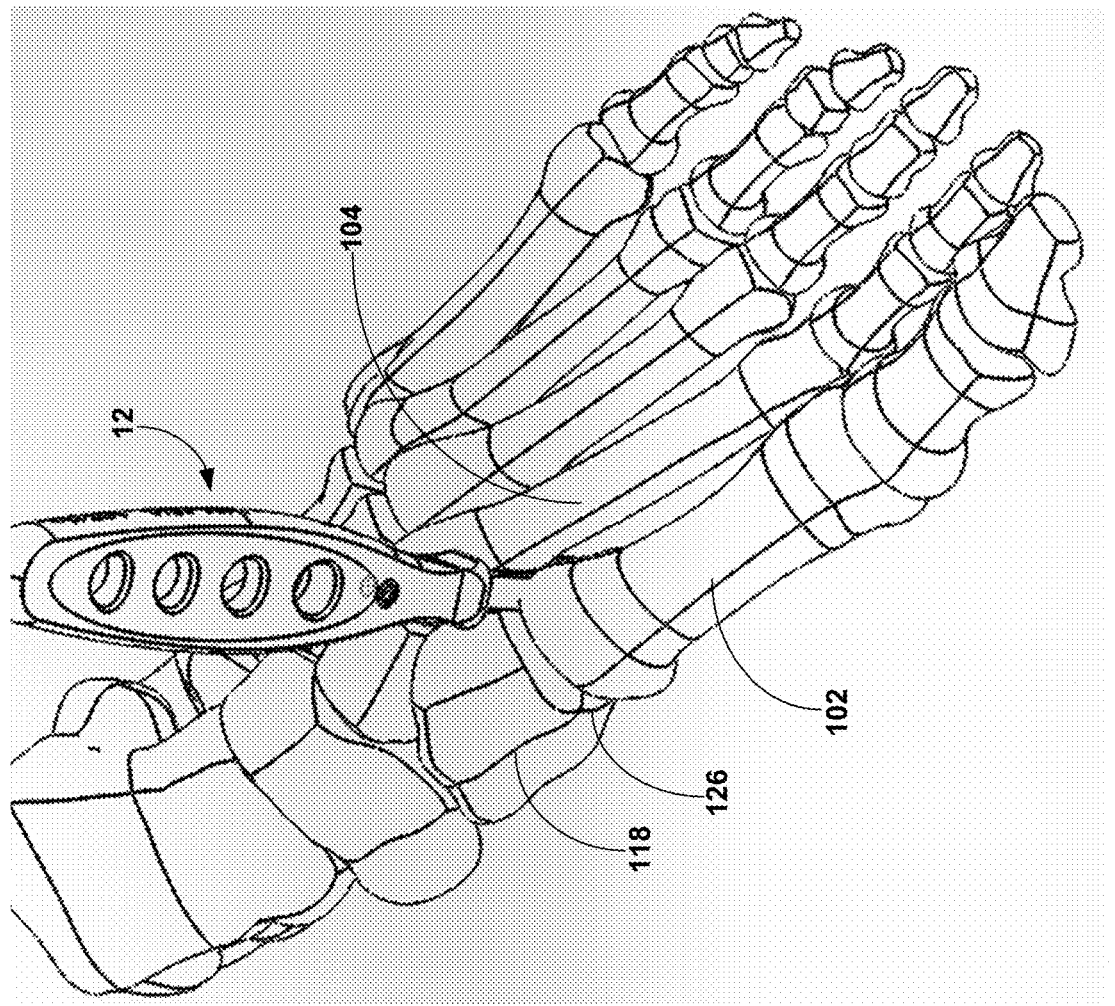

In some applications, the clinician advances cutting head 14 into a first joint space (e.g., tarsometatarsal joint 126), subsequently takes the cutting head out of the joint space, and then inserts the cutting head into a second joint space (e.g., the intermetatarsal joint space). In other applications, the clinician may use one of the side cutting surfaces of cutting head 10 to cut tissue and sweep around the proximal lateral corner of the first metatarsal to transition from the first joint space to the second joint space. FIG. 7E is an illustration of cutting instrument 10 performing an example proximal-lateral cutting sweep around the proximal lateral corner of first metatarsal 102. After performing any desired cutting in the one or more joint spaces, cutting instrument 10 may be removed from the joint space for subsequent steps of the surgical procedure.

Figure 8A:
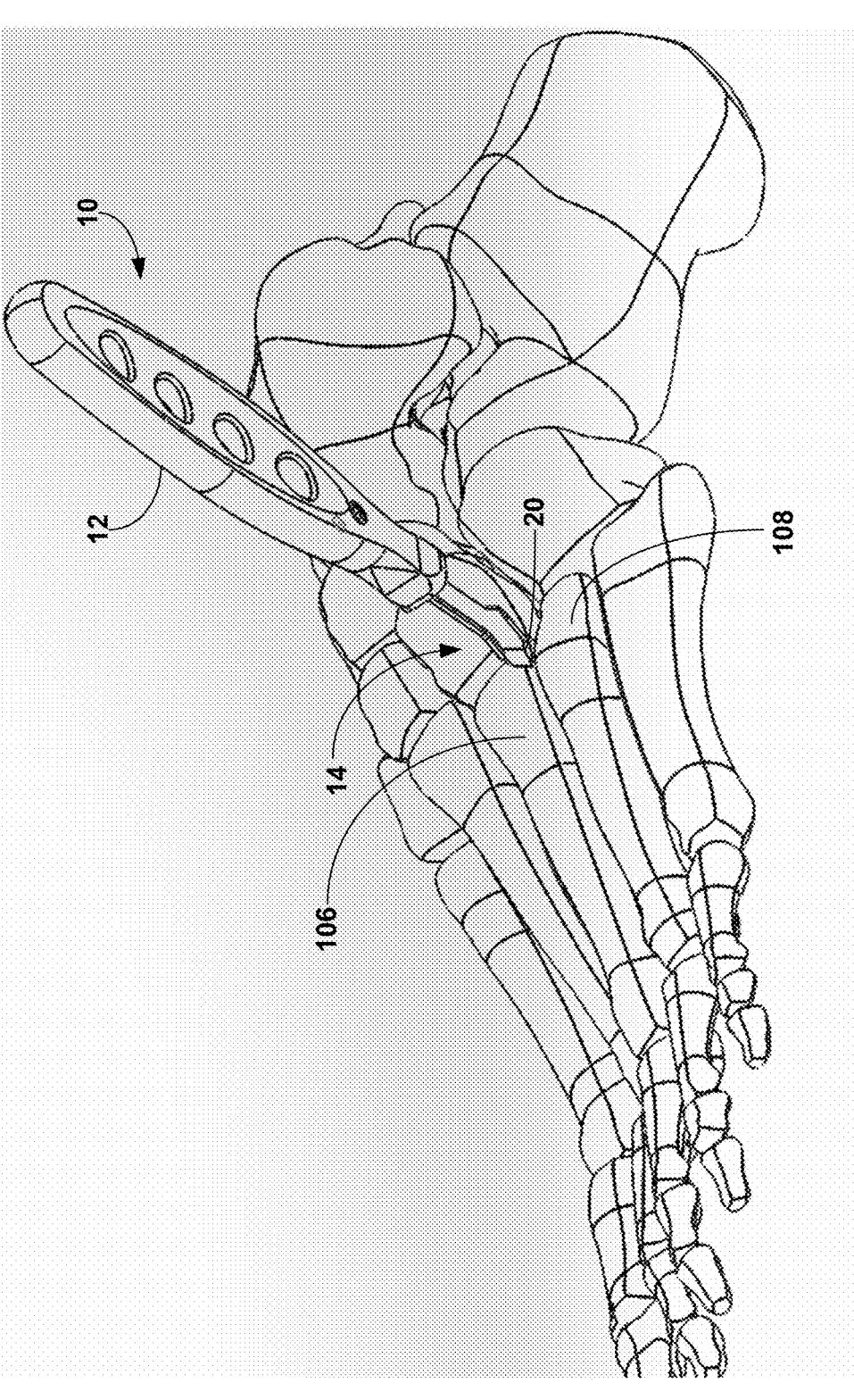
FIGS. 8A and 8B are illustrations of another example joint space in which a cutting instrument according to the disclosure can be inserted and moved to cut tissue for mobilizing a bone for realignment.
Figure 8B:
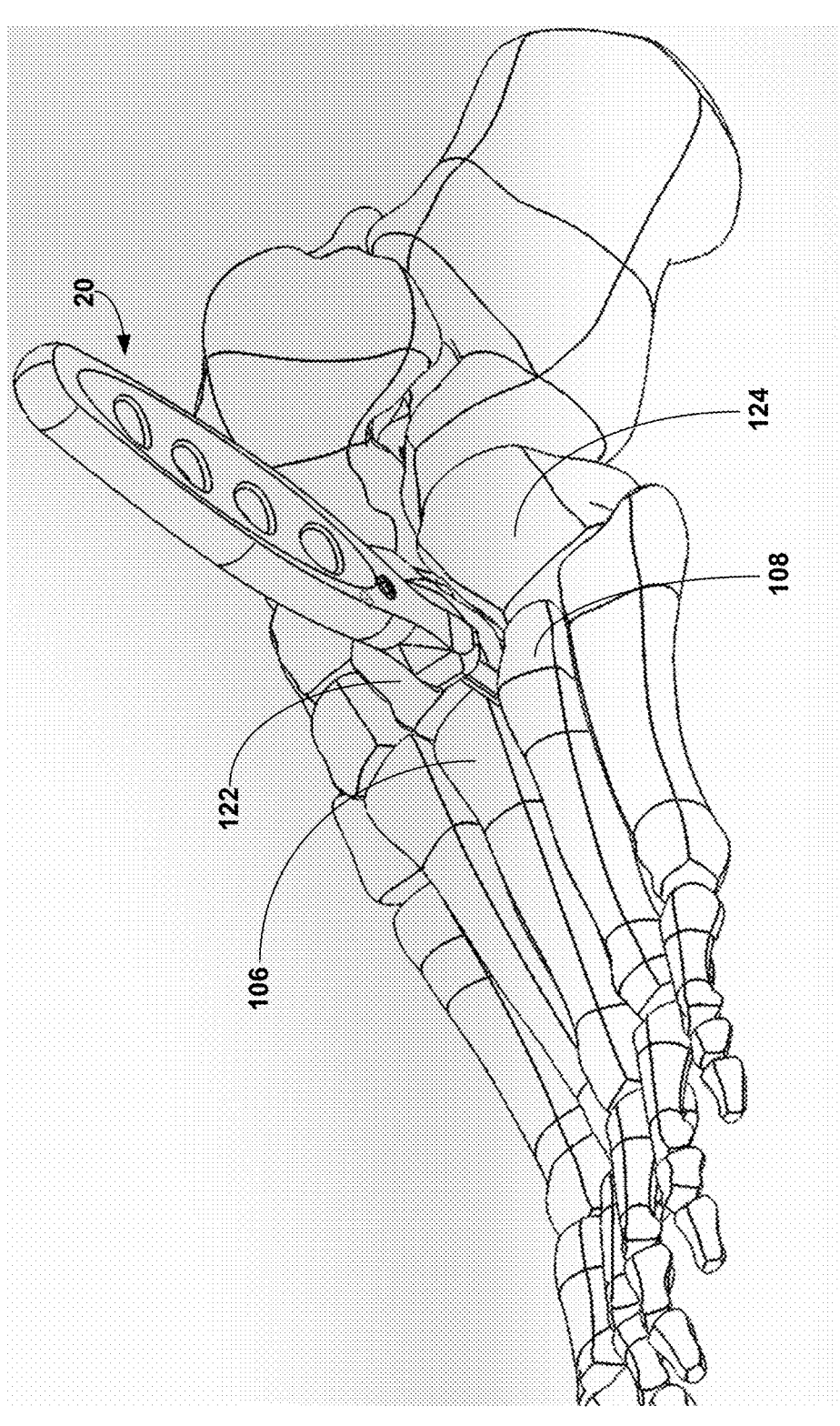

As mentioned above, cutting instrument 10 can be used to cut tissue within a variety of different joint spaces, including different joint spaces within the foot. FIGS. 8A and 8B are illustrations of another example joint space in which cutting instrument 10 can be inserted and moved to cut tissue for mobilizing a bone for realignment. In particular, as seen in FIG. 8A, cutting instrument is illustrated as being insertable into the intermetatarsal space between third metatarsal 106 and fourth metatarsal 108. For example, the clinician may insert cutting head 14 of cutting instrument 10 into the proximal portion of the intermetatarsal space between third metatarsal 106 and fourth metatarsal 108 to cut soft tissue within the joint space. The clinician may cut soft tissue within the joint space to release and mobilize the third metatarsal 106 from fourth metatarsal 108, e.g., to facilitate subsequent realignment of third metatarsal 108 and/or second metatarsal 104, such as in a metatarsus adductus correction procedure.

With reference to FIG. 8A, the clinician can advance the leading cutting surface 20 of cutting head 14 plantarly into the intermetatarsal space between third metatarsal 106 and fourth metatarsal 108. The clinician may introduce cutting head 14 at the proximal base of third metatarsal 106. As shown in FIG. 8B, the clinician can continue plunging the leading cutting surface of cutting head 20 down to a desired depth within the intermetatarsal space. With cutting head 14 at a desired depth in the intermetatarsal space, clinician may sweep cutting instrument 10 in a distal direction (down toward the distal end of the intermetatarsal space away from the cuboid) and/or in a proximal direction (up toward the cuboid) (e.g., in a back-and-forth manner) to cut tissue with the intermetatarsal space using the side cutting surfaces of the cutting instrument.

Figure 8C:
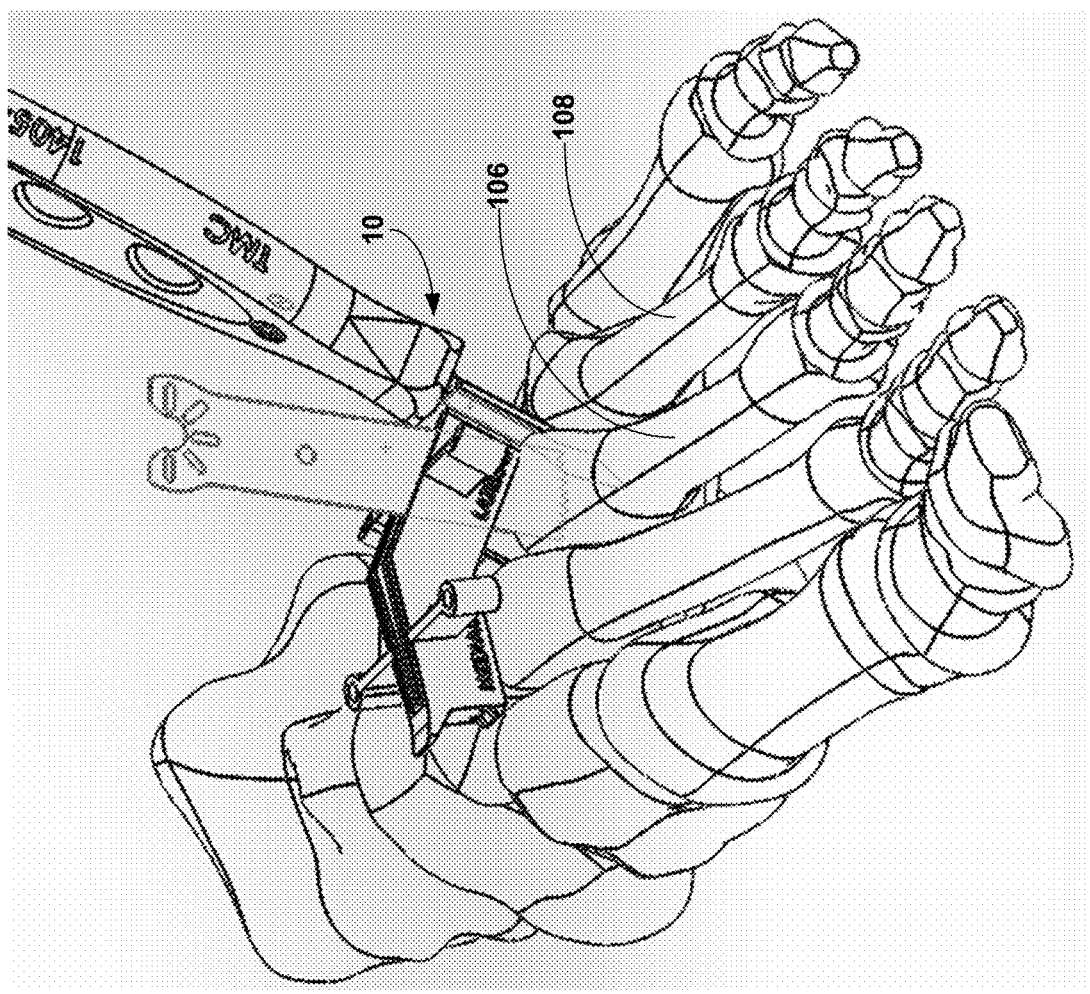
FIG. 8C is an illustration of an example technique using a cutting instrument as a blocking instrument.

With the soft tissue suitably released in the intermetatarsal space, the clinician may remove cutting instrument 10 from the intermetatarsal space. Additionally or alternatively, the clinician may leave cutting instrument 10 in the intermetatarsal space, with handle 12 projecting outwardly from the intermetatarsal space. For example, the clinician may additionally or alternatively utilize cutting instrument 10 as a blocking device to help control subsequent preparation of the end of third metatarsal 106. Cutting instrument 10 may function to help block inadvertently cutting of fourth metatarsal 108 using a saw as the clinician is attempting to prepare the end of third metatarsal 106, optionally using a cut guide. Such a blocking arrangement of cutting instrument 10 is illustrated in FIG. 8C.

With further reference to the example technique of FIG. 6, the technique includes preparing the end of the first bone in the end of the second bone facing the first bone across a joint space for fusion (606). For example, the clinician may prepare an end of a metatarsal being realigned (first metatarsal 102, second metatarsal 104, third metatarsal 106, fourth metatarsal 108, and/or fifth metatarsal 112) and an end of an opposed bone across a tarsometatarsal joint (medial cuneiform 118, intermediate cuneiform 120, lateral cuneiform 122, and/or cuboid bone 124). One or both of the end faces of the metatarsal and the opposed bone can be prepared before and/or after the metatarsal is moved relative to the cuneiform. Accordingly, unless otherwise specified, the order of bone preparation and/or movement is not limited.

In general, the clinician can prepare the end of each bone forming the joint so as to promote fusion of the bone ends across the TMT joint following realignment. Bone preparation may involve using a tissue removing instrument to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. In certain implementations, cutting instrument 10 is used prepare the ends of one or both bone faces in addition to or in lieu of using a different cutting instrument. Such utilization of cutting instrument 10 can be in addition to or in lieu of cutting soft tissue as described herein.

Independent of the type of tissue removing instrument used, the tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand or with the aid of a cutting guide having a guide surface positionable over the portion of bone to be cut. When using a bone preparation guide, a cutting instrument can be inserted against a guide surface (e.g., between a slot define between two guide surfaces) of the bone preparation guide to guide the cutting instrument for bone removal.

The example technique of FIG. 6 also includes realigning at least one bone relative to at least one other bone (608). For example, one or more metatarsals can be a realigned in one or more planes before and/or after preparing one or more end faces of the bones defining the joint. For example, the clinician may move first metatarsal 102, second metatarsal 104, third metatarsal 106, and/or one or more other bones. Moving the bone can include moving the bone in at least one plane. For example, a metatarsal can be moved in at least the transverse plane to close in intermetatarsal angle between the bone being moved in adjacent bone. Additionally or alternatively, the metatarsal may be in the frontal plane (e.g., to reposition the sesamoid bones substantially centered under the metatarsal). In some examples, the metatarsal can be moved in multiple planes, such as the transverse plane and/or frontal plane and/or sagittal plane (e.g., each of the transverse, frontal, and sagittal planes). The clinician may or may not utilize a bone positioning device to facilitate movement of the bone portion. The moved position of the metatarsal can result is realignment of the metatarsal relative to one of more other adjacent bones.

After realignment (or in lieu of performing a separate realignment step), the example technique of FIG. 6 may include compressing one or more bone faces together (610). When performed, the prepared end faces of the bones opposing the joint may be compressed together. The clinician may compress the end faces together with hand pressure and/or using a compressing instrument physically attached to both the first bone portion and the second bone portion.

After suitably realigning one or more of the first, second, third, fourth and/or fifth metatarsals, the technique of FIG. 6 involves fixating the moved position of the one or more moved metatarsals (612). In some examples, a provisional fixation step is performed in which one or more temporary fixation pins are deployed to hold the moved position of one or more metatarsals (e.g., by inserting the fixation pin through one or more moved metatarsal and into one or more adjacent bones). A permanent fixation device can be applied across the joint separating the prepared bone ends to hold a moved position of a bone for subsequent fusion. Example permanent fixation devices include, but are not limited to, pins (e.g., intramedullary nail, K-wire, Steinmann pin), plates, screws, staples, and combinations thereof. With time and healing, the realigned bone can subsequently fuse to the end face of the opposed prepared bone to provide a fused joint.

While cutting instrument 10 has generally been described as an instrument configured with leading cutting surface 20, first side cutting surface 22, and second side cutting surface 24, where the first and second side surfaces extend angularly outwardly from the leading cutting surface. In an alternative configuration of cutting instrument 10, the instrument may be configured with recessed notch at the leading end of cutting head 14. When so configured, the instrument may have a recessed distal cutting surface with first side cutting surface 22 and second side cutting surface 24 extending angularly inwardly to the recessed cutting surface.

Figure 9A:
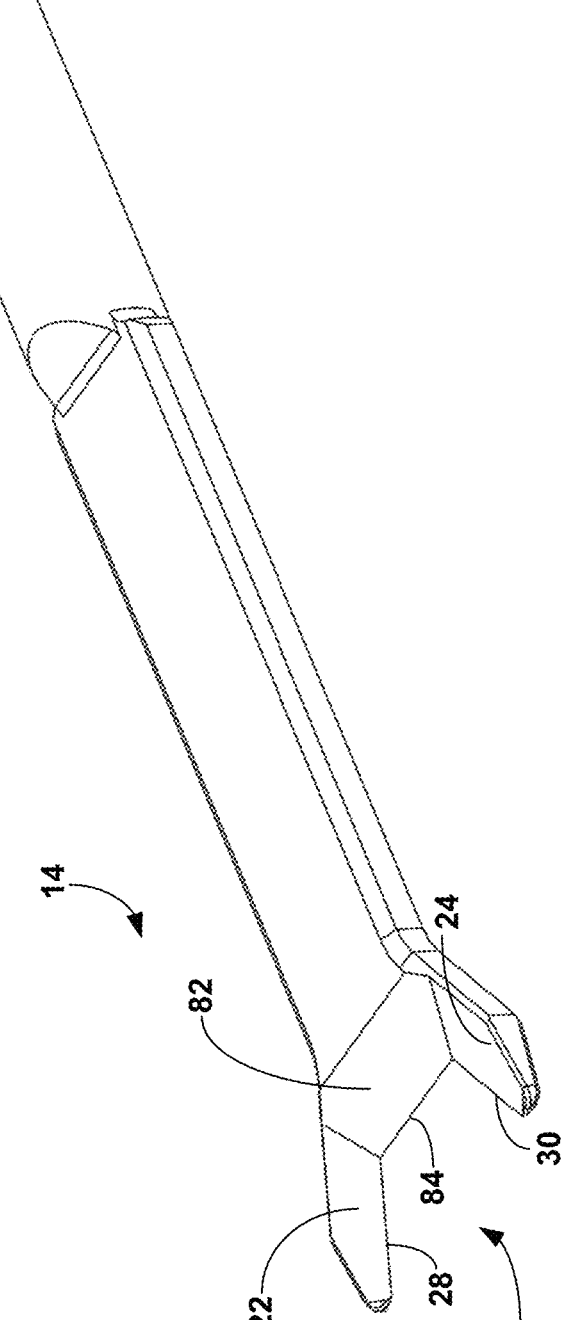
FIGS. 9A and 9B are perspective and top views, respectively, of an alternative example configuration of a cutting head where the cutting head defines a bounded notch or cavity at the distal end of the cutting head
Figure 9B:
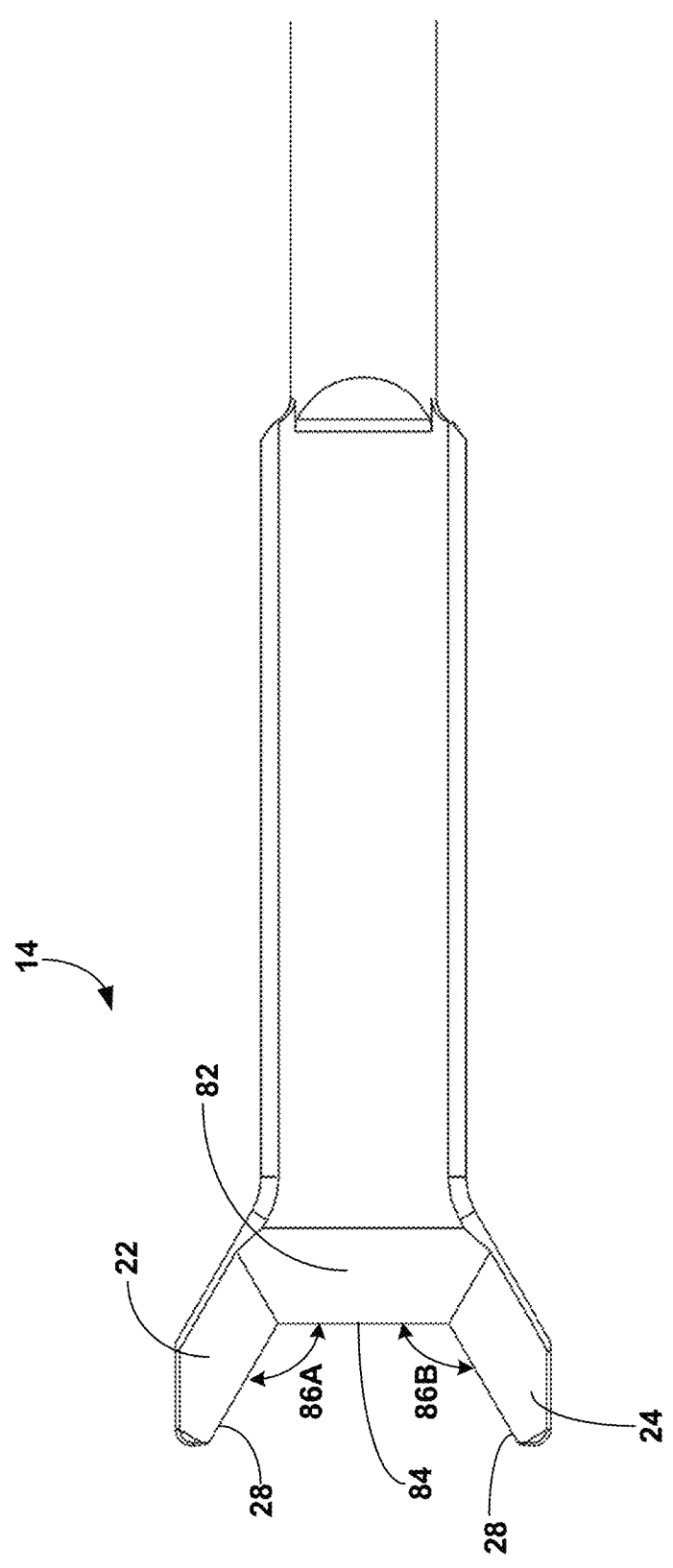

For example, FIGS. 9A and 9B (collectively "FIG. 9") are perspective and top views, respectively, of an alternative example configuration of cutting head 14 of cutting instrument 10 where the cutting head defines a bounded notch or cavity 80 at the distal end of the cutting head. In this example, cutting head 14 has a recessed distal cutting surface 82. First side cutting surface 22 extends angularly inwardly from the distal end of cutting head 14 to recessed distal cutting surface 82. Second side cutting surface 24 also extends angularly inwardly from the distal end of cutting head 14 to recessed distal cutting surface 82. When so configured, cavity 80 can define an inverse shape profile to the shape profile of cutting head 14 described above with respect to FIGS. 1-3.

FIG. 9 illustrates recessed distal cutting surface 82 defining a cutting edge 84, first side cutting surface 22 defining first side cutting edge 28, and second side cutting surface 24 defining second side cutting edge 30. First side cutting surface 22, and first side cutting edge 28 defined thereby, is illustrated as extending angularly away from recessed distal cutting surface 82, and cutting edge 84 defined thereby, in the widthwise direction moving proximally to distally along the length of cutting head 14. Similarly, second side cutting surface 24, and second side cutting edge 30 defined thereby, is illustrated as extending angularly away from recessed distal cutting surface 82, and cutting edge 84 defined thereby, in the widthwise direction moving proximally to distally along the length of cutting head 14. As a result, the overall width of cutting head 14 in the configuration of FIG. 9 enlarges moving from cutting edge 84 of the cutting head distally along the portion of the cutting head defined by first and second side cutting edges 28, 30.

Configuring cutting head 14 with cavity 80 bounded by three cutting edges may be useful to provide a recessed space that a clinician can use to capture and cut tissue. As the clinician advances cutting head 14 toward target tissue to be cut, the clinician can position tissue in cavity 80 of cutting head 14 before further advancing the cutting head to cut the tissue captured in the cavity with one or more cutting surfaces (e.g., cutting edges) of the cutting head.

First side cutting edge 28 can intersect cutting edge 84 of recessed distal cutting surface 82 to define a first intersection angle 86A. Second side cutting edge 30 can intersect cutting edge 84 of recessed distal cutting surface 82 to define a second intersection angle 86B. In some configurations, such as that illustrated in FIG. 9, first intersection angle 86A and second intersection angle 86B may have a same value to provide a symmetrical enlargement of cutting head 14 extending distally outwardly from cutting edge 84. In other configurations, first intersection angle 86A may be different than second intersection angle 86B (e.g., larger or smaller) to provide an asymmetrical profile of cutting head 14. In various examples, first intersection angle 86A and/or second intersection angle 86B may be at least 90 degrees, such as at least 110 degrees, at least 125 degrees, or at least 135 degrees. For example, first intersection angle 86A and/or second intersection angle 86B may range from 90 degrees to 160 degrees, such as from 110 degrees to 145 degrees, or from 115 degrees to 135 degrees.

Cutting head 14 configured according to the example of FIG. 9 can utilize any of the configuration details (e.g., shaped, dimensions) discussed above with respect to cutting head 14 in connection with FIGS. 1-3. For example, recessed distal cutting surface 82 and corresponding cutting edge 84 can be implemented with any of the configuration details described with respect to leading cutting surface 20 and leading cutting edge 26, respectively.

Various examples have been described. These and other examples are within the scope of the following claims.

19

The invention claimed is:

1. An orthopedic cutting instrument comprising:
(a) a handle having a length extending from a first end to a second end; and
(b) a cutting head extending from the second end of the handle, the cutting head comprising:
(i) a leading cutting surface;
(ii) a first side cutting surface extending angularly outwardly from the leading cutting surface on a first side of the cutting head; and
(iii) a second side cutting surface extending angularly outwardly from the leading cutting surface in a direction opposite the first side cutting surface on a second side of the cutting head,
wherein the leading cutting surface defines a trapezoid having a long base, a short base, a first leg joining the long base to the short base, and a second leg joining the long base to the short base, the long base of the trapezoid defining a distal-most end of the cutting head.

2. The instrument of claim 1, wherein:
the cutting head defines a maximum width at a location between the first side cutting surface and the second side cutting surface;
the leading cutting surface terminates in a cutting edge having a length; and
the length of the cutting edge is less than the maximum width of the cutting head.

3. The instrument of claim 2, wherein the cutting edge defines a linear cutting edge.

4. The instrument of claim 2, wherein a ratio of the length of the cutting edge divided by the maximum width of the cutting head ranges from 0.25 to 0.75.

5. The instrument of claim 2, wherein:
the length of the cutting edge ranges from 3 mm to 7 mm; and
the maximum width of the cutting head ranges from 9 mm to 13 mm.

6. The instrument of claim 1, wherein:
the leading cutting surface terminates in a cutting edge extending from a first end to a second end;
the first side cutting surface defines a first angled side edge intersecting the first end of the cutting edge; and
the second side cutting surface defines a second angled side edge intersecting the second end of the cutting edge.

7. The instrument of claim 6, wherein:
the first angled side edge defines a first intersection angle with the first end of the cutting edge, the first intersection angle ranging from 10 degrees to 75 degrees; and
the second angled side edge defines a second intersection angle with the second end of the cutting edge, the second intersection angle ranging from 10 degrees to 75 degrees.

8. The instrument of claim 6, wherein
the first side cutting surface further defines a first straight side edge, the first angled side edge intersecting the first end of the cutting edge on one side and intersecting the first straight side edge on another side; and
the second side cutting surface further defines a second straight side edge, the second angled side edge intersecting the second end of the cutting edge on one side and intersecting the second straight side edge on another side.

9. The instrument of claim 8, wherein the first straight side edge and the second straight side edge are each parallel to a longitudinal axis of the cutting head.

10. The instrument of claim 1, wherein the cutting head further comprises:
a shank;
a first recessed surface extending angularly inwardly from the first side cutting surface to the shank; and
a second recessed surface extending angularly inwardly from the second side cutting surface to the shank.

11. The instrument of claim 10, wherein; the
the first recessed surface defines a first recess intersection angle with the first side cutting surface, the first recessed intersection angle ranging from 10 degrees to 75 degrees; and
the second recessed surface defines a second recessed intersection angle with the second side cutting surface, the second recessed intersection angle ranging from 10 degrees to 75 degrees.

12. The instrument of claim 1, wherein:
the first side cutting surface defines a length parallel to a longitudinal axis of the cutting head;
the second side cutting surface defines a length parallel to the longitudinal axis of the cutting head; and
the length of the first side cutting surface and the length of the second side cutting surface each range from 5 mm to 15 mm.

13. The instrument of claim 1, wherein the cutting head defines a thickness, and the thickness of the cutting head tapers across the leading cutting surface, the first side cutting surface, and the second side cutting surface.

14. The instrument of claim 13, wherein the thickness of the cutting head tapers across the leading cutting surface, the first side cutting surface, and the second side cutting surface at a taper angle ranging from 5 degrees to 25 degrees.

15. The instrument of claim 1, wherein:
the cutting head has a width and a length defining a first side of the cutting head and a second side of the cutting head, the first side of the cutting head being separated from the second side of the cutting head by a thickness of the cutting head;
the leading cutting surface, the first side cutting surface, and the second side cutting surface are each defined on the first side of the cutting head; and
the second side of the cutting head is devoid of cutting surfaces.

16. The instrument of claim 1, wherein:
the cutting head has a width and a length defining a first side of the cutting head and a second side of the cutting head, the first side of the cutting head being separated from the second side of the cutting head by a thickness of the cutting head;
the leading cutting surface comprises a first leading cutting surface on the first side of the cutting head and a second leading cutting surface on the second side of the cutting head, the first and second leading cutting surfaces intersecting each other across the thickness of the cutting head to form a leading cutting edge;
the first side cutting surface comprises two first side cutting surfaces, one on the first side of the cutting head and one on the second side of the cutting head, the two first side cutting surfaces intersecting each other across the thickness of the cutting head to form a first side cutting edge; and
the second side cutting surface comprises two second side cutting surfaces, one on the first side of the cutting head and one on the second side of the cutting head, the two second side cutting surfaces intersecting each other across the thickness of the cutting head to form a second side cutting edge.

17. The instrument of claim 1, wherein:

the cutting head has a width and a length defining the first side of the cutting head and the second side of the cutting head, the first side of the cutting head being separated from the second side of the cutting head by a thickness of the cutting head;

the leading cutting surface, the first side cutting surface, and the second side cutting surface are each defined on the first side of the cutting head; and the cutting head defines a mirrored arrangement of cutting surfaces on the second side of the cutting head.

18. An orthopedic cutting instrument comprising:

(a) a handle having a length extending from a first end to a second end; and (b) a cutting head extending from the second end of the handle, the cutting head comprising:

(i) a leading cutting surface;

(ii) a first side cutting surface extending angularly outwardly from the leading cutting surface on a first side of the cutting head;

(iii) a second side cutting surface extending angularly outwardly from the leading cutting surface in a direction opposite the first side cutting surface on a second side of the cutting head;

(iv) a shank;

(v) a first recessed surface extending angularly inwardly from the first cutting surface to the shank; and (vi) a second recessed surface extending angularly inwardly from the second cutting surface to the shank.

19. The instrument of claim 18, wherein:

the cutting head defines a maximum width at a location between the first side cutting surface and the second side cutting surface;

the leading cutting surface terminates in a cutting edge having a length; and the length of the cutting edge is less than the maximum width of the cutting head.

20. The instrument of claim 18, wherein:

the leading cutting surface terminates in a cutting edge extending from a first end to a second end;

the first side cutting surface defines a first angled side edge intersecting the first end of the cutting edge; and the second side cutting surface defines a second angled side edge intersecting the second end of the cutting edge.

21. The instrument of claim 20, wherein the first side cutting surface further defines a first straight side edge, the first angled side edge intersecting the first end of the cutting edge on one side and intersecting the first straight side edge on another side; and the second side cutting surface further defines a second straight side edge, the second angled side edge intersecting the second end of the cutting edge on one side and intersecting the second straight side edge on another side.

22. The instrument of claim 18, wherein:

the first recessed surface defines a first recess intersection angle with the first side cutting surface, the first recessed intersection angle ranging from 10 degrees to 75 degrees; and the second recessed surface defines a second recessed intersection angle with the second side cutting surface, the second recessed intersection angle ranging from 10 degrees to 75 degrees.

23. The instrument of claim 18, wherein:

the first side cutting surface defines a length parallel to a longitudinal axis of the cutting head;

the second side cutting surface defines a length parallel to the longitudinal axis of the cutting head; and the length of the first side cutting surface and the length of the second side cutting surface each range from 5 mm to 15 mm.

24. The instrument of claim 18, wherein:

the cutting head has a width and a length defining a first side of the cutting head and a second side of the cutting head, the first side of the cutting head being separated from the second side of the cutting head by a thickness of the cutting head;

the leading cutting surface, the first side cutting surface, and the second side cutting surface are each defined on the first side of the cutting head; and the second side of the cutting head is devoid of cutting surfaces.

25. The instrument of claim 18, wherein:

the cutting head has a width and a length defining a first side of the cutting head and a second side of the cutting head, the first side of the cutting head being separated from the second side of the cutting head by a thickness of the cutting head;

the leading cutting surface comprises a first leading cutting surface on the first side of the cutting head and a second leading cutting surface on the second side of the cutting head, the first and second leading cutting surfaces intersecting each other across the thickness of the cutting head to form a leading cutting edge;

the first side cutting surface comprises two first side cutting surfaces, one on the first side of the cutting head and one on the second side of the cutting head, the two first side cutting surfaces intersecting each other across the thickness of the cutting head to form a first side cutting edge; and the second side cutting surface comprises two second side cutting surfaces, one on the first side of the cutting head and one on the second side of the cutting head, the two second side cutting surfaces intersecting each other across the thickness of the cutting head to form a second side cutting edge.

26. An orthopedic cutting instrument comprising:

(a) a handle having a length extending from a first end to a second end; and (b) a cutting head extending from the second end of the handle, the cutting head comprising:

(i) a leading cutting surface terminating in a cutting edge extending from a first end to a second end;

(ii) a first side cutting surface extending angularly outwardly from the leading cutting surface on a first side of the cutting head, wherein the first side cutting surface defines a first angled side edge intersecting the first end of the cutting edge and a first straight side edge, the first angled side edge intersecting the first end of the cutting edge on one side and intersecting the first straight side edge on another side; and (iii) a second side cutting surface extending angularly outwardly from the leading cutting surface in a direction opposite the first side cutting surface on a second side of the cutting head, wherein the second side cutting surface defining a second angled side edge intersecting the second end of the cutting edge and a second straight side edge, the second angled side edge intersecting the second end of the cutting edge on one side and intersecting the second straight side edge on another side.

27. The instrument of claim 26, wherein:

the cutting head defines a maximum width at a location between the first side cutting surface and the second side cutting surface;

the leading cutting surface terminates in a cutting edge having a length; and the length of the cutting edge is less than the maximum width of the cutting head.

28. The instrument of claim 27, wherein a ratio of the length of the cutting edge divided by the maximum width of the cutting head ranges from 0.25 to 0.75.

29. The instrument of claim 26, wherein the first straight side edge and the second straight side edge are each parallel to a longitudinal axis of the cutting head.

30. The instrument of claim 26, wherein:

the cutting head has a width and a length defining a first side of the cutting head and a second side of the cutting head, the first side of the cutting head being separated from the second side of the cutting head by a thickness of the cutting head;

the leading cutting surface, the first side cutting surface, and the second side cutting surface are each defined on the first side of the cutting head; and the second side of the cutting head is devoid of cutting surfaces.

31. The instrument of claim 26, wherein:

the cutting head has a width and a length defining a first side of the cutting head and a second side of the cutting head, the first side of the cutting head being separated from the second side of the cutting head by a thickness of the cutting head;

the leading cutting surface comprises a first leading cutting surface on the first side of the cutting head and a second leading cutting surface on the second side of the cutting head, the first and second leading cutting surfaces intersecting each other across the thickness of the cutting head to form a leading cutting edge;

the first side cutting surface comprises two first side cutting surfaces, one on the first side of the cutting head and one on the second side of the cutting head, the two first side cutting surfaces intersecting each other across the thickness of the cutting head to form a first side cutting edge; and the second side cutting surface comprises two second side cutting surfaces, one on the first side of the cutting head and one on the second side of the cutting head, the two second side cutting surfaces intersecting each other across the thickness of the cutting head to form a second side cutting edge.

* * * * *